US012087432B1

(12) United States Patent
Shiralkar et al.

(10) Patent No.: US 12,087,432 B1
(45) Date of Patent: Sep. 10, 2024

(54) APPARATUS AND METHOD FOR VISUALIZATION OF DIGITIZED GLASS SLIDES BELONGING TO A PATIENT CASE

(71) Applicant: Pramana Inc., Cambridge, MA (US)

(72) Inventors: Manish Shiralkar, Maharashtra (IN); Prasanth Perugupalli, Cary, NC (US); Jithin Prems, Dooravani Nagar (IN); Raghubansh Bahadur Gupta, Bangalore (IN); Durgaprasad Dodle, Telangana (IN); Prateek Jain, Karnataka (IN); Shilpa G Krishna, Kerala (IN); Rohan Prateek, Uttar Pradesh (IN); Priyanka Golchha, Rajasthan (IN); Jaya Jain, Bhopal (IN); Asa Rubin, Silver Springs, MD (US); Parveen Shaik Gangirevula, Bengaluru (IN)

(73) Assignee: Pramana, Inc., Cambridge, MA (US)

( * ) Notice: Subject to any disclaimer, the term of this patent is extended or adjusted under 35 U.S.C. 154(b) by 0 days.

(21) Appl. No.: 18/229,812

(22) Filed: Aug. 3, 2023

(51) Int. Cl.
*G16H 30/40* (2018.01)
*G06T 15/00* (2011.01)
*G06V 10/24* (2022.01)
*G06V 10/74* (2022.01)
*G16H 30/20* (2018.01)

(52) U.S. Cl.
CPC .............. *G16H 30/40* (2018.01); *G06T 15/00* (2013.01); *G06V 10/24* (2022.01); *G06V 10/761* (2022.01); *G16H 30/20* (2018.01)

(58) Field of Classification Search
CPC ........ G16H 30/20; G16H 30/40; G06T 15/00; G06V 10/24; G06V 10/761
See application file for complete search history.

(56) References Cited

U.S. PATENT DOCUMENTS 9,501,844 B2 * 11/2016 Young .................. G06V 20/69
11,538,162 B2  12/2022 Gorton
(Continued)

FOREIGN PATENT DOCUMENTS

WO  WO-2019046774 A1 *  3/2019  ............... G01N 1/30

*Primary Examiner* — Nay A Maung
*Assistant Examiner* — Jose M Torres
(74) *Attorney, Agent, or Firm* — Caldwell Intellectual Property Law

(57) ABSTRACT

An apparatus for visualization of digitized glass slides belonging to a patient case having a processor and a memory communicatively connected to the processor, the memory containing instructions configuring the processor to receive an image data set having a plurality of images of one or more specimen and metadata of the plurality of images of the one or more specimen, identify one or more constituent virtualization components for each image of the plurality of images within image data set, determine a relationship between the one or more constituent visualization components as a function of the image data set, construct a plurality of virtual images as a function of the image data set and the relationship between the one or more virtual constituent components, wherein each of plurality of the images includes at least one virtual constituent component generate a consolidated virtual image as a function of the plurality of virtual images and display the consolidated virtual image.

18 Claims, 10 Drawing Sheets

(56) References Cited

U.S. PATENT DOCUMENTS

| | | | | |
|---|---|---|---|---|
| 2003/0123717 A1* | 7/2003 | Bacus | .................... | G16H 30/20 |
| | | | | 382/128 |
| 2013/0162805 A1* | 6/2013 | Takayama | ............ | G02B 21/365 |
| | | | | 348/80 |
| 2021/0192729 A1* | 6/2021 | Raciti | .................... | G06V 10/82 |
| 2023/0131675 A1 | 4/2023 | Kunz | | |
| 2023/0411014 A1* | 12/2023 | Olson | .................... | G16H 50/70 |

* cited by examiner

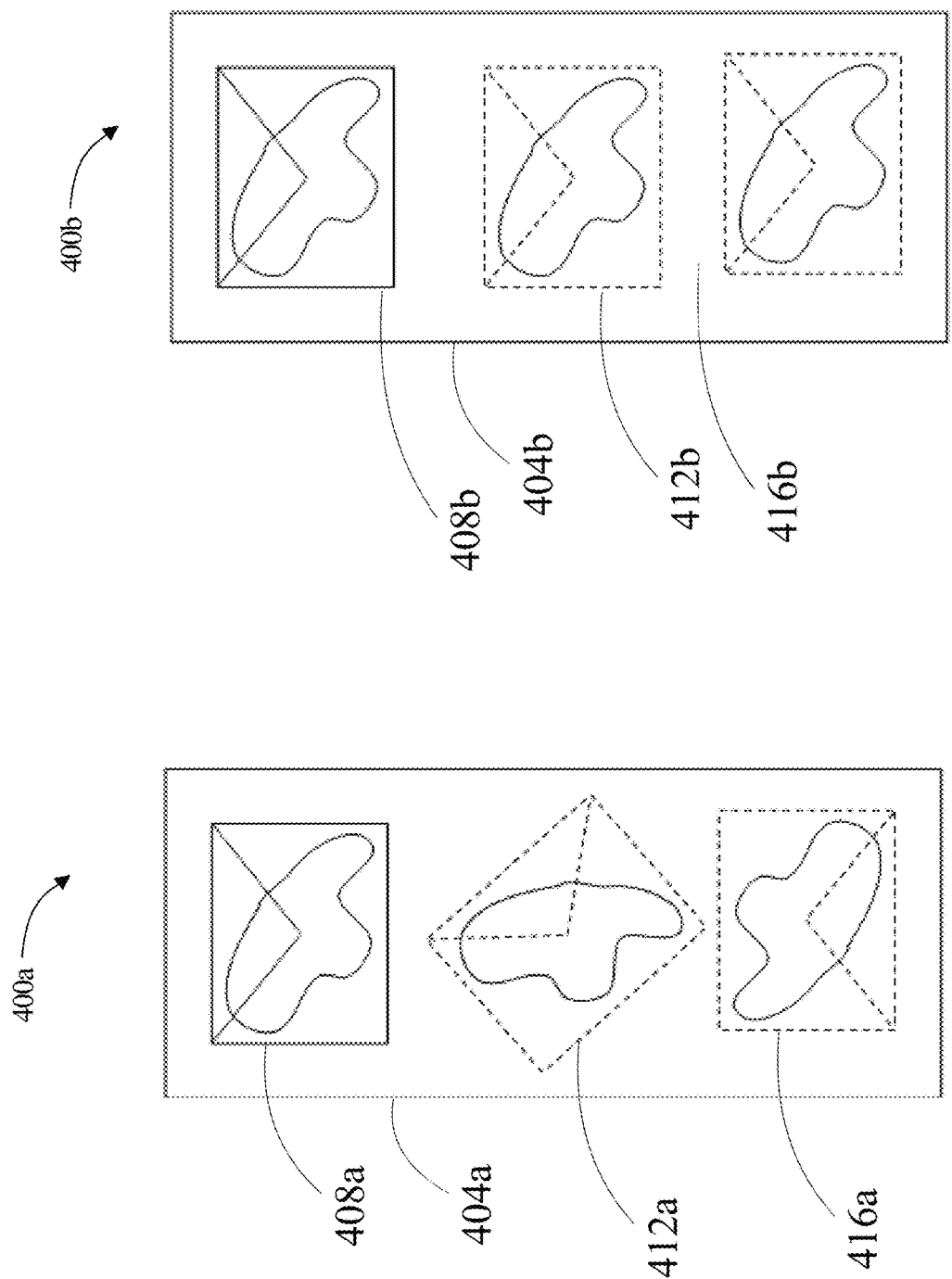

APPARATUS AND METHOD FOR VISUALIZATION OF DIGITIZED GLASS SLIDES BELONGING TO A PATIENT CASE

FIELD OF THE INVENTION

The present invention generally relates to the field of image generation. In particular, the present invention is directed to visualization of digitized slides relating to a patient case.

BACKGROUND

The placement of a specimen on glass slides may result in air bubbles or other unwanted materials that distract from the specimen that is to be observed. In addition, the digitization of glass slides may result in related specimens having differing size characteristics or differing orientations. Current systems utilized to visualize glass slides do not provide for modification of glass slides in order to remove any unwanted material. In addition, current systems utilized to visualize glass slides do not provide for proper modification of the glass slides in reference to one or more specimens contained on the slides.

SUMMARY OF THE DISCLOSURE

In an aspect, an apparatus for visualization of digitized glass slides belonging to a patient case is described. Apparatus includes a processor and a memory communicatively connected to the processor, the memory containing instructions configuring the processor to receive an image data set having a plurality of images of one or more specimen and metadata of the plurality of images of the one or more specimen, identify one or more constituent virtualization components for each image of the plurality of images within image data set, determine a relationship between the one or more constituent visualization components as a function of the image data set, construct a plurality of virtual images as a function of the image data set and the relationship between the one or more virtual constituent components, wherein each of plurality of the images includes at least one virtual constituent component generate a consolidated virtual image as a function of the plurality of virtual images and display the consolidated virtual image.

In another aspect, a method for visualization of digitized glass slides belonging to a patient case is described. The method includes receiving, by at least a processor, an image data set including a plurality of images of one or more specimen and metadata of the plurality of images of the one or more specimen, identifying, by the at least a processor, one or more constituent virtualization components for each image of the plurality of images within image data set, determining, by the at least a processor, a relationship between the one or more constituent visualization components as a function of the image data set. constructing, by the at least a processor, a plurality of virtual images as a function of the image data set and the relationship between the one or more virtual constituent components, wherein each of plurality of the images includes at least one virtual constituent component, generating, by the at least a processor, a consolidated virtual image as a function of the plurality of virtual images, and displaying, by the at least a processor, the consolidated virtual image.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A-B are yet another exemplary embodiment of images and corresponding virtual images that have been modified through one or more processes as described with respect to FIG. 1;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for visualization of digitized glass slides. In an embodiment, apparatus includes a processor and a memory. In one or more embodiments, apparatus may include optical sensors, machine vision systems, macro cameras and the like.

1 Aspects of the present disclosure can be used to modify digitized glass slides to create virtual images of the glass slides. Aspects of the present disclosure can also be used to modify the placement of specimens on glass slides. Aspects of this disclosure can also be used to remove any unwanted empty space within an image and/or any annotations within an image. Exemplary embodiments illustrating aspects of the present disclosure are described below in the context of several specific examples.

Figure 1:
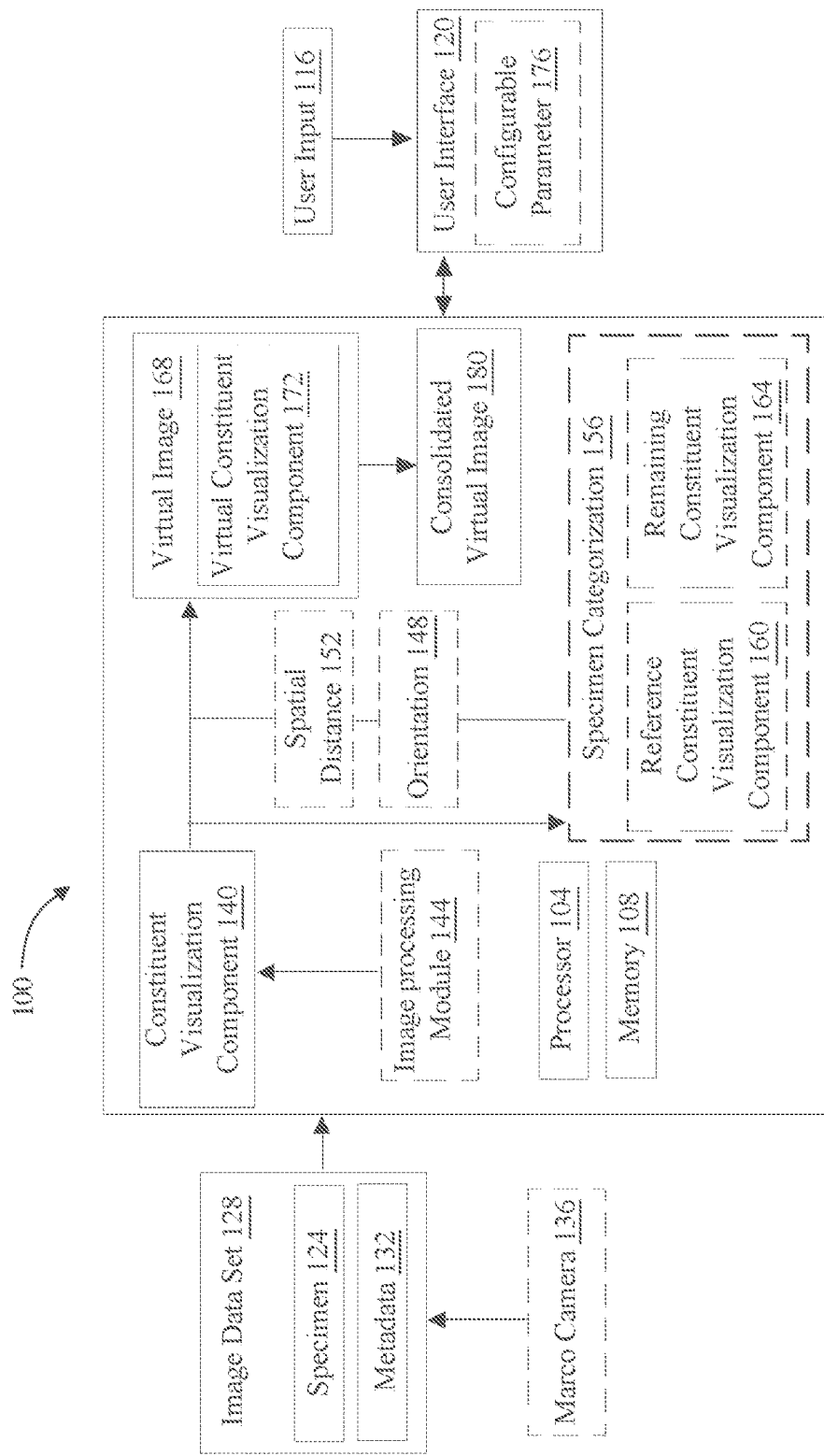
FIG. 1 is a block diagram of an exemplary embodiment of an apparatus for visualization of digitized glass slides.

Referring now to FIG. 1, an exemplary embodiment of apparatus 100 for visualization of glass slides belonging to a patient case is described. In one or more embodiments, apparatus 100 may include an optical instrument. For instance, and without limitation, apparatus 100 may include a microscope. In one or more embodiments, apparatus 100 may include an application-specific integrated circuit (ASIC). ASIC may be communicatively connected to a memory, such as memory 108. Memory may include rea-only memory (ROM) and/or rewritable ROM, FPGA, or other combinational and/or sequential synchronous or non-synchronous digital circuitry to store parameters described further in this disclosure. In one or more embodiments, memory may include one or more memory devices to store data and information, such as parameters or metrics. The one or more memory devices may include various types of memory including, but not limited to, volatile and non-volatile memory devices, such as, for example, ROM (Read-Only Memory), EEPROM (Electrically Erasable Read-Only Memory), RAM (Random Access Memory), flash memory, and the like. In one or more embodiments, embodiment, processor 104 is adapted to execute software stored in memory to perform various methods, processes, and modes of operations in manner as described in this disclosure. In other embodiments, apparatus 100 may include circuitry. For instance, and without limitation, apparatus 100 may include programming in software and/or hardware circuit design. In one or more embodiments, apparatus 100 may include a processor 104. Processor 104 may include, without limitation, any processor 104 described in this disclosure. Processor 104 may include or be included in any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes memory 108. Memory 108 is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, imaging device, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, apparatus 100 may include one or more sensors for capturing image signals representative of an image of a scene (e.g., a scene including a specimen). For instance, and without limitation, a sensor may include a light sensor, image sensor (as described further below), focal plane array, and the like. In various embodiments, sensors may provide for representing and/or converting a captured image signal of a scene to digital data. For instance, and without limitation, sensor may include an analog-to-digital converter. In one or more embodiments, processor 104 may be adapted to receive image signals from apparatus 100 (e.g., image sensor), process image signals to provide processed image data, store image signals and/or image data in memory 108, and/or retrieve stored image signals and/or image data from memory 108 (e.g., for compilation or combinations as discussed further in this disclosure). In one or more embodiments, processor 104 may be configured to process image signals stored in memory 108 to provide image data to display for viewing by a user and/or operator.

Figure 10:
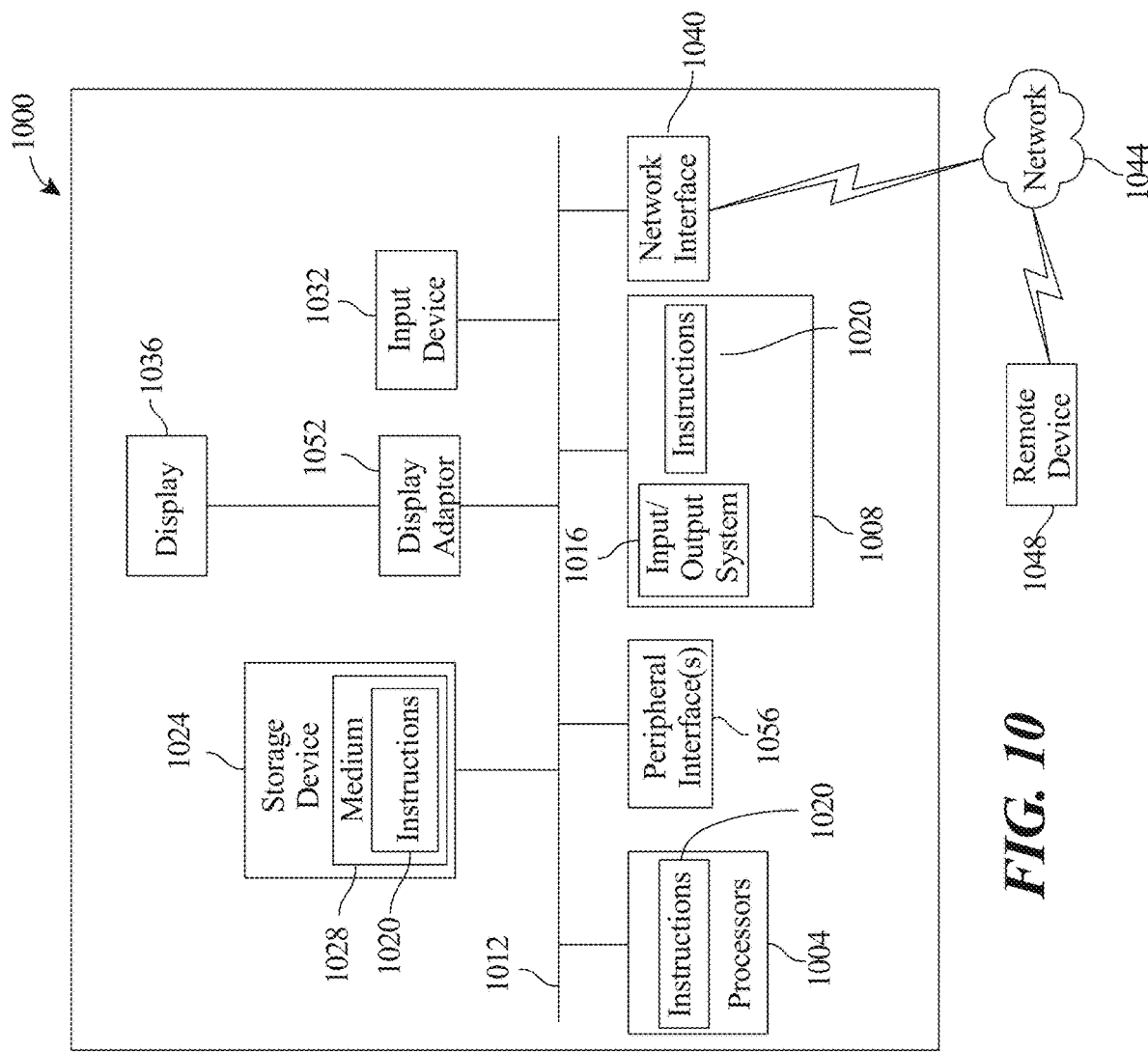
FIG. 10 is a block diagram of a computing system that can be used to implement any one or more of the methodologies disclosed herein and any one or more portions thereof.

Still referring to FIG. 1, in one or more embodiments, apparatus 100 may include and/or be communicatively connected to a display, which is discussed further in FIG. 10. In one or more embodiments, display may be configured to display image data and any other information described in this disclosure, such as annotations or text. In one or more embodiments, processor 104 may be configured to retrieve image data and information from memory 108 and display such image data and information on display. In other embodiments, display may receive image data directly from optical system, such as optical system (e.g., optical sensor).

Still referring to FIG. 1, apparatus 100 may include a user input 116 and/or user interface 120. "User input" for the purposes of this disclosure is a datum received as a function of an interaction between a user and a computing device. For example, user input 116 may include the slicking of a mouse, the selection of a key on a keyboard and any other interactions within input devices that may connected to a computing device. A "user interface" is a means by which a user and a computer system interact. For instance, and without limitation, user interface 120 may include one or more user actuated components, such as, for example, one or more push buttons, joysticks, slide bars, rotatable knobs, a mouse, a keyboard, touchscreens, and the like that may be configured to generate one or more input control signals, where an input control signal may include a signal to capture an image from a scene, combine images and/or image data, compile images and/or image data, alter modes of operation of imaging device, alter zoom and/or levels of zoom, alter focus, and the like. User input 116 signals may be generated using user interface 120 and transmitted to processor 104, memory 108, display, optical system, and/or any other component of and/or communicatively connected to apparatus 100. In one or more embodiments, processor 104 may be configured to alter or set modes of operation of imaging device, such as but not limited to, autofocus, contrast, gain (e.g., variable gain), field of view (FOV), brightness, offset, menu enablement and selection, spatial setting, temporal setting, and the like.

With continued reference to FIG. 1, in some embodiments, apparatus 100 may be used to generate one or more images of a specimen 124. For the purposes of this disclosure, a "specimen" is a sample of organic material used for testing or observation purposes. In one or more embodiments, specimen 124 may include a pathology sample. For instance, and without limitation, a specimen 124 may include a sample of interest, including tissue, plasma, or fluid from an individual. For example, and without limitation, specimen 124 may include tissue from an organ, such as a kidney, of an individual (e.g., patient). In some embodiments, specimen 124 may include a tissue sample. In some embodiments, specimen 124 may be frozen. In some embodiments, specimen 124 may be fresh or recently harvested. In one or more embodiments, specimen 124 may include a variable thickness. For instance, and without limitation, specimen 124 may have a different thickness or depth at various locations along specimen 124. For example, and without limitation, specimen 124 may have a first thickness t at a first location x, a second thickness t' at a second location x', and a third thickness t" at a third location x".

With continued reference to FIG. 1, in one or more embodiments, specimen 124 may be disposed on a slide. As used in this disclosure, a "slide" is a container or surface for holding specimen 124. In some embodiments, slide may include a formalin fixed paraffin embedded slide. In some embodiments, specimen 124 on slide may be stained. In some embodiments, slide may be substantially transparent. In some embodiments, slide may include a glass slide. In some embodiments, slide may include a thin, flat, and substantially transparent glass slide. In some embodiments, a cover, such as a transparent cover, may be applied to slide such that specimen 124 is disposed between slide and cover. For example, and without limitation, specimen 124 may be compressed between slide and corresponding cover.

Still referring to FIG. 1, in some embodiments, slide and/or a sample on slide may be illuminated. In some embodiments, apparatus 100 may include a light source. As used in this disclosure, a "light source" is any device configured to emit electromagnetic radiation. In some embodiments, light source may emit a light having substantially one wavelength. In some embodiments, light source may emit a light having a wavelength range. Light source may emit, without limitation, ultraviolet light, visible light, and/or infrared light. In non-limiting examples, light source may include a light-emitting diode (LED), an organic LED (OLED) and/or any other light emitter. Such a light source may be configured to illuminate slide and/or specimen 124 on slide. In a non-limiting example, light source may illuminate slide and/or specimen 124 on slide from below. In a non-limiting example, light source may illuminate slide and/or specimen 124 on slide from above.

Still referring to FIG. 1, in some embodiments, apparatus 100 may include at least an optical system. As used in this disclosure, an "optical system" is an arrangement of one or more components which together act upon or employ electromagnetic radiation, such as light. Light may include visible light, infrared light, UV light, or the like. Optical system may include one or more optical elements, including without limitation lenses, mirrors, windows, filters, and the like. Optical system may form an optical image that corresponds to an optical object. For instance, and without limitation, optical system may form an optical image at or upon an optical sensor, which can capture, e.g., digitize, the optical image. In some cases, optical system may have at least a magnification. For instance, and without limitation, optical system may include an objective (e.g., microscope objective) and one or more reimaging optical elements that together produce an optical magnification. In some cases, a degree of optical magnification may be referred to herein as zoom. As used herein, an "optical sensor" is a device that measures light and converts the measured light into one or more signals; one or more signals may include, without limitation, one or more electrical signals. In some embodiments, optical sensor may include at least a photodetector. As used herein, a "photodetector" is a device that is sensitive to light and thereby able to detect light. In some embodiments, a photodetector may include a photodiode, a photoresistor, a photosensor, a photovoltaic chip, and the like. In some embodiments, optical sensor may include a plurality of photodetectors. Optical sensor may include, without limitation, a camera. Optical sensor may be in electronic communication with at least a processor 104 of apparatus 100. As used herein, "electronic communication" as used in this disclosure is a shared data connection between two or more devices. In some embodiments, apparatus 100 may include two or more optical sensors.

Still referring to FIG. 1, in some embodiments, optical system may include a camera. In some cases, a camera may include one or more optics. Exemplary non-limiting optics include spherical lenses, aspherical lenses, reflectors, polarizers, filters, windows, aperture stops, and the like. In some embodiments, one or more optics associated with a camera may be adjusted in order to, in non-limiting examples, change the zoom, depth of field, and/or focus distance of the camera. In some embodiments, one or more of such settings may be configured to detect a feature of a sample on slide. In some embodiments, one or more of such settings may be configured based on a parameter set, as described below. In some embodiments, camera may capture images at a low depth of field. In a non-limiting example, camera may capture images such that a first depth of sample is in focus and a second depth of sample is out of focus. In some embodiments, an autofocus mechanism may be used to determine focus distance. In some embodiments, focus distance may be set by parameter set. In some embodiments, camera may be configured to capture a plurality of images at different focus distances. In a non-limiting example, camera may capture a plurality of images at different focus distances, such that images are captured where each focus depth of the sample is in focus in at least one image. In some embodiments, at least a camera may include an image sensor. Exemplary non-limiting image sensors include digital image sensors, such as without limitation charge-coupled device (CCD) sensors and complimentary metal-oxide-semiconductor (CMOS) sensors. In some embodiments, a camera may be sensitive within a non-visible range of electromagnetic radiation, such as without limitation infrared.

Still referring to FIG. 1, in some embodiments, apparatus 100 may include a machine vision system. Machine vision system may include optical system or may be communicatively connected to optical system, processor 104, memory 108, and the like. In some embodiments, a machine vision system may include at least a camera. A machine vision system may use images, such as images from at least a camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z-axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy-plane of a first frame; a result, x and y translational components and $\phi$ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy-plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure. A z-axis, as used in this disclosure, is an axis that is orthogonal to the xy-plane and, thus, a top surface of slide.

With continued reference to FIG. 1, optical system may be configured to capture an image of an area of interest. For example, and without limitation, a camera of optical system may be configured to capture an image of an area of interest. For the purposes of this disclosure, an "area of interest" is a region of a scene or environment that is selected or desired to be positioned within a line of sight and, thus, a Field of view of an optical component of an optical system. An "line of sight", for the purposes of this disclosure, is a line along which an observer or lens has unobstructed vision. A "field of view", for the purposes of this disclosure, is an angle through and/or an area within which an optical component detects electromagnetic radiation. For instance, and without limitation, FOV may indicate an area of a scene that may be captured by an optical component within defined bounds (e.g., a frame) of an image. For example, and without limitation, an area of interest within FOV of optical system may include a scene desired to be captured in an image by being placed within a line of sight of a lens of optical system, so that image may be captured. FOV may include vertical and horizontal angles that project relative to the surface of a lens of an optical component. In one or more embodiments, line of sight may include an optical access of the FOV. In various embodiments, an area of interest may include at least a portion of specimen 124. In some embodiments, an area of interest may include a portion of specimen 124 and a portion of slide.

Still referring to FIG. 1, in one or more embodiments, image may include image data. As used in this disclosure, "image data" is information representing at least a physical scene, space, and/or object. Image data may include, for example, information representing a sample, slide, or region of a sample or slide. In some cases, image data may be generated by a camera. "Image data" may be used interchangeably through this disclosure with "image," where image is used as a noun. An image may be optical, such as without limitation where at least an optic is used to generate an image of an object. An image may be digital, such as without limitation when represented as a bitmap. Alternatively, an image may be comprised of any media capable of representing a physical scene, space, and/or object. Alternatively, where "image" is used as a verb, in this disclosure, it refers to generation and/or formation of an image.

With continued reference to FIG. 1, apparatus 100 is configured to receive an image data set 128. "Image data set" for the purposes of this disclosure is a collection of images, for instance that represent one or more captured specimen 124. In some cases, images data set may include one or more images, or a plurality of images, of one or more specimen 124 that is to be examined. In some cases, the images may depict one or more specimens 124 on slide. In some cases, image data set 128 may further include metadata 132 of the plurality of images. "Metadata" for the purposes of this disclosure is information that is used to describe other data. For example, metadata 132 may include information of one or more images. In some cases, metadata 132 may include the date and time an image was taken, the information of the one or more sensors or cameras used to capture the image, the location of the image, various image compression formats used on the image and the like. In some cases, metadata 132 may further include information about a particular specimen 124 within the image. This may include but is not limited to the type of specimen 124, such as the tissue the specimen 124 has been retrieved from, the date the specimen 124 was retrieved, the location of the specimen 124 on the tissue (e.g. such as on an X-y coordinate system), the boundaries of the specimen 124, (e.g. such as on an X-Y coordinate system), a particular boundary that may include specimen 124 (e.g. such as an area that specimen 124 is contained within), whether the specimen 124 is associated to other specimens 124 that are retrieved from the same tissue block (e.g. one of many specimens 124 retrieved from a particular tissue block such as a heart), the location of the specimen 124 on the tissue block (e.g. A1, wherein 'A' may denote the first row and '1' may denote the first column or vice versa), the preservation conditions (e.g. refrigeration needed, one or more preservation chemicals needed, etc.) and the like. In some cases, metadata 132 may include information such as the collection notes of a particular specimen 124 within the image, the order in which the image was received (e.g. metadata 132 indicating that a particular image was the first image taken) and the like. In some cases, metadata 132 may include the size of the specimen 124 and the like. In some cases, image data set 128 may include information about one or more specimens 124. In some cases, image data may include captured slides of one or more specimens 124. In some cases, image data set 128 may include digitized glass slides. "Digitized glass slides" for the purposes of this disclosure are slides that have been captured using one or more input sensors and/or optical sensors and converted into a digital format.

With continued reference to FIG. 1, in some cases, each image within image data set 128 may include an image of a glass slide, wherein the glass slide is a thin rectangular piece of glass containing specimen 124. In some cases, the glass slide may include more than one specimen 124. In some cases, more than one specimen 124 on each glass slide may be associated with one another. For example, more than one specimen 124 may be retrieved from the same tissue block, wherein a first specimen 124 on glass slides may be associated with a first layer, a second specimen 124 on the glass slide may be associated with a second layer and so on. In some cases, metadata 132 may include the location of specimen 124 on the glass block.

With continued reference to FIG. 1, in some cases, apparatus 100 may receive image data set 128 through the use of one or more optical sensors and/or optical systems as described above. In some cases, apparatus 100 may be configured to receive image data set 128 from a macro camera 136. "Macro camera" for the purposes of this disclosure is a specialized camera used for close-up photography. Macro camera 136 may allow an individual to capture images of smaller objects such as specimen 124 with great detail. Macro camera 136 may use one or more macro lenses, wherein the macro lenses allow an individual to focus on an object that is within close proximity. In some cases, macro lenses have a magnification ratio of 1:1 or higher. In some cases, macro lenses may allow for capturing or an image from a distance of 12 inches or less. In some cases, images captured may a macro camera 136 may be larger than the object captured. In some cases, macro camera 136 may be used to capture images with high detail such as specimen 124, that may be used to examine specimen 124. In some cases, apparatus 100 may be communicatively connected to a camera such as macro camera 136. In some cases, macro camera 136 may include an ordinary camera that contains a macro lens. In some cases, image data set 128 may be received by macro camera 136, wherein macro camera 136 may be configured to capture at least one macro image of a particular slide of a specimen 124 to be used in examination. In some cases, metadata 132 may include information about one or more images captured by macro camera 136.

Still referring to FIG. 1, in some embodiments, apparatus 100 may include a user interface 120, as previously described in this disclosure. User interface 120 may include output interface and input interface. In some embodiments, output interface may include one or more elements through which apparatus 100 may communicate information to a user. In a non-limiting example, output interface may include a display. A display may include a high-resolution display. A display may output images, videos, and the like to a user. In another non-limiting example, output interface may include a speaker. A speaker may output audio to a user. In another non-limiting example, output interface may include a haptic device. A speaker may output haptic feedback to a user.

Still referring to FIG. 1, in some embodiments, input interface may include controls for operating apparatus 100 and/or inputting data into apparatus 100. Such controls may be operated by a user. Input interface may include, in non-limiting examples, a camera, microphone, keyboard, touch screen, mouse, joystick, foot pedal, button, dial, and the like. Input interface may accept, in non-limiting examples, mechanical input, audio input, visual input, text input, and the like. In some embodiments, audio inputs into input interface may be interpreted using an automatic speech recognition function, allowing a user to control imaging device 100 via speech. In some embodiments, input interface may approximate controls of a microscope. In some cases, image data set 128 may be received through input interface. For example, a user may input one or more images through a user interface 120. In some cases, apparatus 100 may be configured to receive image data set 128 from an imaging device as described in U.S. Non provisional application Ser. No. 18/226,058, filed on Jul. 25, 2023 and entitled "IMAGING DEVICE AND A METHOD FOR IMAGE GENERATION OF A SPECIMEN" the entirety of which is incorporated herein by reference. In some cases, one or more images may be received from imaging device and received as an element of image data set 128.

Still referring to FIG. 1, in one or more embodiments, apparatus 100 may be configured to create multi-layer scan, where the multi-layer scan includes a plurality, such as a series, of images combined into a single image. A multi-layer scan may include an integrated image. For instance, and without limitation, multi-layer scan includes a compilation of consecutive images taken at different levels along a z-axis, or depth axis, at a particular location (x, y) of specimen 124. For instance, and without limitation, multi-layer scan may include a plurality of images including an image taken with a focus depth A, an image taken with a focus depth B, and image taken with a focus depth C, and so on, as discussed further below.

With continued reference to FIG. 1, apparatus 100 and/or processor 104 is configured to determine for each image the plurality of images within image data set 128, the membership of a set of images for visualization as a function of image data set 128. "Membership" for the purposes of this disclosure is a commonality that may be shared between one or more specimens 124 in an image or between one or more images. For example, membership may include a determination of two images containing specimens 124 from the same block. Similarly, membership may include a determination of the similarity or commonality of two specimens 124 that are captured within a singular photo. For example, two specimens 124 from the same photo may share a commonality wherein they are retrieved from the same block. Alternatively two specimens 124 may not share a commonality such that they are retrieved from the same tissue block. In some cases, each slide may contain more than one specimen 124. In some cases, membership may include images taken within a similar time frame, images containing similarly categorized specimens 124 (e.g. categorization of heart tissue specimens 124, lung tissue specimens 124, and the like). In some cases, membership may include a numerical membership wherein a particular image was taken prior to another image.

With continued reference to FIG. 1, apparatus 100 and/or processor 104 may be configured to determine a membership of a set of images, wherein the set of images may include images sharing a particular commonality. In some cases, image data set 128 may contain more than one set of images wherein each set of images may share a particular membership. In some cases, each set of images may include images of specimens 124 taken from the same tissue block. In some cases, processor 104 may determine the membership of a set of images as function of metadata 132. In some cases, each image within image data set 128 may include metadata 132, wherein the metadata 132 include information about particular specimen 124 wherein processor 104 may be configured to categorize each specimen 124. In some cases, metadata 132 may include the order in which an image was taken wherein processor 104 may create an order of images within image data set 128 wherein the first image is associated to the first image that was captured and the last image is associated to the last image captured. In some cases, processor 104 may determine for each image, a membership between one or more images for visualization. In some cases, processor 104 may categorize images for visualization wherein a particular set of images may be viewed consecutively. In some cases, determining a membership may allow for visualizing more than one images that are associated with the same of similar specimen 124. In some cases, determining membership may allow for viewing one or more images simultaneously through a display as described in this disclosure.

With continued reference to FIG. 1, apparatus 100 may be configured to determine a relationship between one or more constituent visualization components 140 as a function of the image data set 128. In some cases, apparatus 100 may determine a relationship by determining whether two specimens 124 are from the same class (e.g. both specimens 124 contain heart tissue). In some cases, apparatus 100 may determine a relationship between two specimens 124 that came from the same tissue block. In some cases, apparatus 100 may determine that two specimens 124 may need to be observed in relation to one another based on user input 116. In some cases, processor 104 may identify one or more constituent visualization components 140 within an image and determine a relationship between them. In some cases, apparatus 100 and/or processor 104 may be configured to identify one or more constituent visualization components 140 with a particular image or multiple images wherein apparatus 100 may be configured to determine a relationship between two or more specimens 124. In some cases, a relationship may be determined based on metadata 132 or any other information within image data set 128. In some cases, metadata 132 may indicate that an image contains more than one specimen 124 and the source of the specimens 124. In some cases, apparatus 100 may be configured to pair up and/or categorize specimens 124 that are related to one another, such as specimens 124 that contain layers of a particular tissue.

With continued reference to FIG. 1, determining a relationship may include identifying one or more constituent visualization components 140 within image data set 128. apparatus 100 and/or processor 104 may be configured to identify one or more constituent visualization components 140 within image data set 128. "Constituent visualization components" for the purposes of this disclosure are objects represented within each image, for instance within image data set 128. For example, constituent visualization components 140 may include specimens 124 located on the slides. In some cases, constituent visualization components 140 may further include debris, annotations, air bubbles, unwanted visible particles captured within the image, an adhesive used to adhere two slides together and the like. In some cases, constituent visualization components 140 may include an object within a particular image. In some cases, a user may annotate a particular specimen 124 wherein processor 104 may identify the annotation as a constituent visualization component 140. In some cases, an image may capture specimen 124 as well as debris wherein the specimen 124 and the debris are identified as virtual constituent components. In some cases, processor 104 may be configured to identify one or more constituent visualization components 140 within an image using metadata 132. In one or more embodiments, a particular image may contain metadata 132 of the location and/or the borders of a particular specimen 124. In one or more embodiments, metadata 132 may include information indicating the presence of one or more specimens 124 within an image. In one or more embodiments, metadata 132 may indicate the borders and/or location of one or more specimens 124. In some cases, metadata 132 may include information associated with annotations, debris and other constituent visualization components 140. In some cases, another computing device separate and distinct from apparatus 100 may have been configured to generate metadata 132, wherein the metadata 132 may include information about the one or more virtual constituent components.

With continued reference to FIG. 1, in some cases, identifying one or more constituent visualization components 140 includes determining a light intensity of one or more portions of an image. "Light intensity" for the purposes of this disclosure is a value that denotes that amount of light in a particular pixel. In some cases, light intensity may include a range of 0 to 255 wherein a score of zero may indicate that the pixel contains no light and therefore nay be visualized as black, and a score of 255 indicates maximum light wherein the pixel may be visualized as white. In one or more embodiments, a particular specimen 124 may be captured relative to a white or lighted surface wherein the presence of pixels with lower light intensities may indicate the presence of a specimen 124 or other constituent visualization components 140. In an embodiment, an image within image data set 128 may be captured in front of the lighted surface, such as a white colored surface or a transparent surface having a light emitting device beneath the surface. In an embodiment, image may contain lower light intensities in areas that contain constituent visualization components 140. Alternatively, image may be captured behind a low light intensive surface such as a black surface, wherein the presence of light intensity may indicate the presence of a particular constituent visualization component 140. In one or more embodiments, each image within image data set 128 may include a plurality of pixels wherein each pixel may contain a pixel value. The pixel value may indicate the light intensity of the pixel within a particular portion of the image. In some cases, images may be in grayscale wherein each pixel contains a value of 0 to 255 wherein a value of zero indicates that the pixel represents a completely black portion of an image and a value of 255 indicates that that pixel represents a completely white portion of the image. In some cases, an image may contain a color image wherein the image is depicted in red, green and blue (RGB) value wherein a particular value of red, a particular value of green and a particular value of blue may be used to visualize a particular color on display. For example, a color such as yellow may contain an RGB value of (255,255,0) wherein the first 255 indicates the intensity of red, the second 255 indicates the intensity of green, and the 0 indicates the intensity of blue. In some cases, processor 104 may be configured to determine the light intensity of an image through RGB values wherein an RGB value of (0,0,0) may indicate the portion of image is white and therefore contains a large light intensity and an RGB value of (255,255,255) may indicate a portion of an image is black and therefore contains a lower light intensity. In some cases, image may include the Hugh, saturation and value (known as 'HSL' or alternatively 'HSL' which corresponds to high, saturation and lightness) wherein the value or the lightness may be used to determine the intensity of a particular pixel in an image.

With continued reference to FIG. 1, in some cases, identifying one or more constituent visualization components 140 may include determining the light intensity of one or more images. In some cases the presence of particular light intensities or ranges may indicate the presence of one or more constituent visualization components 140. In some cases, a particular range of light intensities may indicate the presence of one or more constituent visualization components 140. For example, processor 104 may determine the presence of one or more light intensities on an image having a white background. In some cases, the presence of a particular light intensity below a particular threshold (e.g. 245) may indicate the particular portion of the image contains a particular constituent visualization component 140. In some cases, identifying one or more constituent visualization components 140 may include identifying one or more portions of an image containing higher or lower light intensities in comparison to the background of the image. In some cases, computing device may distinguish between two constituent visualization components 140 by the relative size or ranges of light intensities. For example, a particular portion of an image may contain light intensities of within a given range and another portion of an image may include light intensities within a differing given range wherein processor 104 may determine that the two portions of the image are differing constituent visualization components 140. In some cases, processor 104 may determine the size of a particular grouping of pixels within image, wherein the size is determined by pixels grouped near each other having differing light intensities. For example, a particular portion of an image may include a grouping of pixels having lower light intensities wherein a length (wherein length is denoted in the x direction on an XY axis, or the height (wherein the height is denoted in the Y direction on an XY axis) of the constituent visualization components 140 may be measured from a first pixel on a plane containing a differing light intensity to the last pixel on the plane containing a differing light intensity. For example, the length of the constituent visualization component 140 may be determined by identifying a first pixel on a particular XY axis having a particular light intensity and identifying the last pixel on the same Y axis along the X axis that contains the same or similar light intensity. In an embodiment, the borders of a particular constituent visualization component 140 may be identified based on the changes in light intensity between the borders of the constituent visualization components 140 and the corresponding background of the image. In some cases, processor 104 may determine the relative size of each constituent visualization components 140 by measuring the largest length within the grouping of pixels, the largest height within the grouping of pixels and/or the area of the grouping of pixels. In some cases, size may be measured in relation to the overall size of the photo wherein each pixel may represent a particular unit (e.g. a 100×100 pixel of a photo containing metadata 132 that the photo represents a 4 inch by 4-inch scene may be used to indicate that each pixel represents 4/100 of an inch). In some cases, processor 104 may determine the difference between constituent visualization components 140 based on their respective sizes within an image. For example, a small grouping of pixels may indicate that the constituent visualization component 140 is debris or dirt, wherein a large grouping of pixels may indicate that the constituent visualization component 140 may be specimen 124. In some cases, processor 104 may distinguish between constituent visualization components 140 using light intensities wherein a particular range of light intensities may indicate a particular constituent visualization component 140. For example, specimen 124 may be represented by a grouping of pixels having lower light intensities wherein an air bubble may be visualized by pixels having high light intensities. In some cases, processor 104 may distinguish between two or more constituent visualization components 140 based on the presence of a particular range of light intensities between two groupings of pixels having similar light intensities. For example, a first grouping of pixels containing lower light intensities may be separated from a second grouping of pixels having lower light intensities by a plurality of pixels having higher light intensities between the first grouping of pixels and the second grouping of pixels. In an embodiment the presence of a particular size or grouping of pixels having higher light intensities may indicate a separation between a first constituent visualization component 140 and a second constituent visualization components 140. In some cases, processor 104 may be configured to ignore variations in light intensities within given regions of an image such as the borders of an image wherein the borders may contain differing light intensities due to issues with image capture.

With continued reference to FIG. 1, apparatus 100 may include an image processing module 144. As used in this disclosure, an "image processing module" is a component designed to process digital images. For example, and without limitation, image processing, module may be configured to compile plurality of images of a multi-layer scan to create an integrated image. In an embodiment, image processing module 144 may include a plurality of software algorithms that can analyze, manipulate, or otherwise enhance an image, such as, without limitation, a plurality of image processing techniques as described below. In another embodiment, image processing module 144 may slow include hardware components such as, without limitation, one or more graphics processing units (GPUs) that can accelerate the processing of large number of images. In some cases, image processing module 144 may be implemented with one or more image processing libraries such as, without limitation, OpenCV, PIL/Pillow, ImageMagick, and the like. image processing module 144 may include, be included in, or be communicatively connected to optical system, processor 104, and/or memory.

Still referring to FIG. 1, image processing module 144 may be configured to receive images from processor 104 and/or any other input methods as described herein. In a non-limiting example, image processing module 144 may be configured to receive images by generating a first image capture parameter, transmitting a command to optical system to take first image of a plurality of images with the first image capture parameter, generate a second image capture parameter, transmit a command to optical system to take second image of a plurality of images with the second image capture parameter, and receive, from optical system, first image and second image. In another non-limiting example, plurality of images may be taken by optical system using the same image capture parameter. Image capture parameter may be generated as a function of user input 116 or processor 104.

Still referring to FIG. 1, plurality of images from image data set 128 may be transmitted from processor 104 to image processing module 144 via any suitable electronic communication protocol, including without limitation packet-based protocols such as transfer control protocol-internet protocol (TCP-IP), file transfer protocol (FTP) or the like. Receiving images may include retrieval of images from a data store containing images as described below; for instance, and without limitation, images may be retrieved using a query that specifies a timestamp that images may be required to match.

Still referring to FIG. 1, image processing module 144 may be configured to process images. In an embodiment, image processing module 144 may be configured to compress and/or encode images to reduce the file size and storage requirements while maintaining the essential visual information needed for further processing steps as described below. In an embodiment, compression and/or encoding of plurality of images may facilitate faster transmission of images. In some cases, image processing module 144 may be configured to perform a lossless compression on images, wherein the lossless compression may maintain the original image quality of images. In a non-limiting example, image processing module 144 may utilize one or more lossless compression algorithms, such as, without limitation, Huffman coding, Lempel-Ziv-Welch (LZW), Run-Length Encoding (RLE), and/or the like to identify and remove redundancy in each image in a plurality of images without losing any information. In such embodiment, compressing and/or encoding each image of a plurality of images may include converting the file format of each image into PNG, GIF, lossless JPEG2000 or the like. In an embodiment, images compressed via lossless compression may be perfectly reconstructed to the original form (e.g., original image resolution, dimension, color representation, format, and the like) of images. In other cases, image processing module 144 may be configured to perform a lossy compression on plurality of images, wherein the lossy compression may sacrifice some image quality of images to achieve higher compression ratios. In a non-limiting example, image processing module 144 may utilize one or more lossy compression algorithms, such as, without limitation, Discrete Cosine Transform (DCT) in JPEG or Wavelet Transform in JPEG2000, discard some less significant information within images, resulting in a smaller file size but a slight loss of image quality of images. In such embodiment, compressing and/or encoding each image of a plurality of images may include converting the file format of each image into JPEG, WebP, lossy JPEG2000, or the like.

Still referring to FIG. 1, in an embodiment, processing images may include determining a degree of quality of depiction of a region of interest of an image or a plurality of images. In an embodiment, image processing module 144 may determine a degree of blurriness of images. In a non-limiting example, image processing module 144 may perform a blur detection by taking a Fourier transform, or an approximation such as a Fast Fourier Transform (FFT) of images and analyzing a distribution of low and high frequencies in the resulting frequency-domain depiction of images; for instance, and without limitation, numbers of high-frequency values below a threshold level may indicate blurriness. In another non-limiting example, detection of blurriness may be performed by convolving images, a channel of images, or the like with a Laplacian kernel; for instance, and without limitation, this may generate a numerical score reflecting a number of rapid changes in intensity shown in each image, such that a high score indicates clarity, and a low score indicates blurriness. In some cases, blurriness detection may be performed using a Gradient-based operator, which measures operators based on the gradient or first derivative of images, based on the hypothesis that rapid changes indicate sharp edges in the image, and thus are indicative of a lower degree of blurriness. In some cases, blur detection may be performed using Wavelet-based operator, which takes advantage of the capability of coefficients of the discrete wavelet transform to describe the frequency and spatial content of images. In some cases, blur detection may be performed using statistics-based operators take advantage of several image statistics as texture descriptors in order to compute a focus level. In other cases, blur detection may be performed by using discrete cosine transform (DCT) coefficients in order to compute a focus level of images from its frequency content. Additionally, or alternatively, image processing module 144 may be configured to rank images according to degree of quality of depiction of a region of interest and select a highest-ranking image from a plurality of images.

Still referring to FIG. 1, processing images may include enhancing at least a region of interest via a plurality of image processing techniques to improve the quality (or degree of quality of depiction) of an image for better processing and analysis as described further in this disclosure. In an embodiment, image processing module 144 may be configured to perform a noise reduction operation on an image, wherein the noise reduction operation may remove or minimize noise (arises from various sources, such as sensor limitations, poor lighting conditions, image compression, and/or the like), resulting in a cleaner and more visually coherent image. In some cases, noise reduction operation may be performed using one or more image filters; for instance, and without limitation, noise reduction operation may include Gaussian filtering, median filtering, bilateral filtering, and/or the like. Noise reduction operation may be done by image processing module 144, by averaging or filtering out pixel values in neighborhood of each pixel of an image to reduce random variations.

Still referring to FIG. 1, in another embodiment, image processing module 144 may be configured to perform a contrast enhancement operation on an image. In some cases, an image may exhibit low contrast, which may, for example, make a feature difficult to distinguish from the background. Contrast enhancement operation may improve the contrast of an image by stretching the intensity range of the image and/or redistributing the intensity values (i.e., degree of brightness or darkness of a pixel in the image). In a non-limiting example, intensity value may represent the gray level or color of each pixel, scale from 0 to 255 in intensity range for an 8-bit image, and scale from 0 to 16,777,215 in a 24-bit color image. In some cases, contrast enhancement operation may include, without limitation, histogram equalization, adaptive histogram equalization (CLAHE), contrast stretching, and/or the like. image processing module 144 may be configured to adjust the brightness and darkness levels within an image to make a feature more distinguishable (i.e., increase degree of quality of depiction). Additionally, or alternatively, image processing module 144 may be configured to perform a brightness normalization operation to correct variations in lighting conditions (i.e., uneven brightness levels). In some cases, an image may include a consistent brightness level across a region after brightness normalization operation performed by image processing module 144. In a non-limiting example, image processing module 144 may perform a global or local mean normalization, where the average intensity value of an entire image or region of an image may be calculated and used to adjust the brightness levels.

Still referring to FIG. 1, in other embodiments, image processing module 144 may be configured to perform a color space conversion operation to increase degree of quality of depiction. In a non-limiting example, in case of a color image (i.e., RGB image), image processing module 144 may be configured to convert RGB image to grayscale or HSV color space. Such conversion may emphasize the differences in intensity values between a region or feature of interest and the background. image processing module 144 may further be configured to perform an image sharpening operation such as, without limitation, unsharp masking, Laplacian sharpening, high-pass filtering, and/or the like. image processing module 144 may use image sharpening operation to enhance the edges and fine details related to a region or feature of interest within an image by emphasizing high-frequency components within an image.

Still referring to FIG. 1, processing images may include isolating a region or feature of interest from the rest of an image as a function of plurality of image processing techniques. Images may include highest-ranking image selected by image processing module 144 as described above. In an embodiment, plurality of image processing techniques may include one or more morphological operations, wherein the morphological operations are techniques developed based on set theory, lattice theory, topology, and random functions used for processing geometrical structures using a structuring element. A "structuring element," for the purpose of this disclosure, is a small matrix or kernel that defines a shape and size of a morphological operation. In some cases, structing element may be centered at each pixel of an image and used to determine an output pixel value for that location. In a non-limiting example, isolating a region or feature of interest from an image may include applying a dilation operation, wherein the dilation operation is a basic morphological operation configured to expand or grow the boundaries of objects (e.g., a cell, a dust particle, and the like) in an image. In another non-limiting example, isolating a region or feature of interest from an image may include applying an erosion operation, wherein the erosion operation is a basic morphological operation configured to shrink or erode the boundaries of objects in an image. In another non-limiting example, isolating a region or feature of interest from an image may include applying an opening operation, wherein the opening operation is a basic morphological operation configured to remove small objects or thin structures from an image while preserving larger structures. In a further non-limiting example, isolating a region or feature of interest from an image may include applying a closing operation, wherein the closing operation is a basic morphological operation configured to fill in small gaps or holes in objects in an image while preserving the overall shape and size of the objects. These morphological operations may be performed by image processing module 144 to enhance the edges of objects, remove noise, or fill gaps in a region or feature of interest before further processing.

Still referring to FIG. 1, in an embodiment, isolating a region or feature of interest from an image may include utilizing an edge detection technique, which may detect one or more shapes defined by edges. In one or more embodiments, the feature or region of interest includes the one or more constituent visualization components 140. In some cases, each constituent visualization component 140 may include a region or feature of interest. An "edge detection technique," as used in this disclosure, includes a mathematical method that identifies points in a digital image, at which the image brightness changes sharply and/or has a discontinuity. In an embodiment, such points may be organized into straight and/or curved line segments, which may be referred to as "edges." Edge detection technique may be performed by image processing module 144, using any suitable edge detection algorithm, including without limitation Canny edge detection, Sobel operator edge detection, Prewitt operator edge detection, Laplacian operator edge detection, and/or Differential edge detection. Edge detection technique may include phase congruency-based edge detection, which finds all locations of an image where all sinusoids in the frequency domain, for instance as generated using a Fourier decomposition, may have matching phases which may indicate a location of an edge. Edge detection technique may be used to detect a shape of a feature of interest such as a cell, indicating a cell membrane or wall; in an embodiment, edge detection technique may be used to find closed figures formed by edges.

Referring to FIG. 1, in a non-limiting example, identifying one or more constituent visualization components 140 may include isolating one or more features of interests using one or more edge detection techniques. A feature of interest may include a specific area within a digital image that contains information relevant to further processing, such as one or more constituent visualization components 140. In a non-limiting example, image data located outside a feature of interest may include irrelevant or extraneous information. Such portion of an image containing irrelevant or extraneous information may be disregarded by image processing module 144, thereby allowing resources to be concentrated at a feature of interest. In some cases, feature of interest may vary in size, shape, and/or location within an image. In a non-limiting example feature of interest may be presented as a circle around the nucleus of a cell. In some cases, feature of interest may specify one or more coordinates, distances, and the like, such as center and radius of a circle around the nucleus of a cell in an image. image processing module 144 may then be configured to isolate feature of interest from the image based on feature of interest. In a non-limiting example, image processing module 144 may crop an image according to a bounding box around a feature of interest.

Still referring to FIG. 1, image processing module 144 may be configured to perform a connected component analysis (CCA) on an image for feature of interest isolation. As used in this disclosure, a "connected component analysis (CCA)," also known as connected component labeling, is an image processing technique used to identify and label connected regions within a binary image (i.e., an image which each pixel having only two possible values: 0 or 1, black or white, or foreground and background). "Connected regions," as described herein, is a group of adjacent pixels that share the same value and are connected based on a predefined neighborhood system such as, without limitation, 4-connected or 8-connected neighborhoods. In some cases, image processing module 144 may convert an image into a binary image via a thresholding process, wherein the thresholding process may involve setting a threshold value that separates the pixels of an image corresponding to feature of interest (foreground) from those corresponding to the background. Pixels with intensity values above the threshold may be set to 1 (white) and those below the threshold may be set to 0 (black). In an embodiment, CCA may be employed to detect and extract feature of interest by identifying a plurality of connected regions that exhibit specific properties or characteristics of the feature of interest. image processing module 144 may then filter plurality of connected regions by analyzing plurality of connected regions properties such as, without limitation, area, aspect ratio, height, width, perimeter, and/or the like. In a non-limiting example, connected components that closely resemble the dimensions and aspect ratio of feature of interest may be retained, by image processing module 144 as feature of interest, while other components may be discarded. image processing module 144 may be further configured to extract feature of interest from an image for further processing as described below.

With continued reference to FIG. 1, in some cases, processor 104 and/or image processing module 144 may be configured to identify one or more constituent visualization components 140 using an image classifier. Processor 104 may use an image classifier to classify images or portions thereof within image data set 128. An "image classifier," as used in this disclosure is a machine-learning model, such as a mathematical model, neural net, or program generated by a machine-learning algorithm known as a "classification algorithm," as described in further detail below, that sorts inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. processor 104 and/or another computing device may generate image classifier using a classification algorithm, defined as a process whereby processor 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, processor 104 may use an image classifier to identify one or more key images in data described in any data described in this disclosure. As used herein, a "key image" is an element of visual data used to identify and/or match elements to each other. An image classifier may be trained with binarized visual data that has already been classified to determine key images in any other data described in this disclosure. "Binarized visual data" for the purposes of this disclosure is visual data that is described in binary format. For example, binarized visual data of a photo may be comprised of ones and zeroes wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g. image data set 128) described in this disclosure and output one or more key images within the data. As used herein, a "key image" is an element of visual data used to identify and/or match elements to each other. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Classifiers as described throughout this disclosure may be configured to output at least a datum that labels or otherwise identifies a set of data that are clustered together, found to be close under a distance metric as described below, or the like.

With continued reference to FIG. 1, processor 104 may be configured to generate classifiers as described throughout this disclosure using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process for the purposes of this disclosure. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors for the purposes of this disclosure may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, in an embodiment, image classifier may be used to compare visual data in data such as image data set 128 with visual data in another data set. Visual data in another data set may include a plurality of visual data retrieved from database. In some cases, image classifier may classify portions of one or more images within image data set 128. In some cases, image classifier may identify one or more constituent visualization components 140 within one or more images within image data set 128. In some cases, image classifier may determine a relationship between two or more constituent visualization components 140. For example, image classifier may be used to determine that two constituent visualization components 140 contain specimens 124 retrieved from the same block. In some cases, image classifier may identify two related constituent visualization components 140 and their corresponding orientation 148 to one another. For example, a particular specimen 124 may be orientated a at a particular angle in reference to another specimen 124. In some cases, image classifier may be used to distinguish between specimens 124 and other constituent visualization components 140 that are not of interest. In some cases, image classifier may be used to determine the edges or boundaries of one or more constituent visualization components 140.

With continued reference to FIG. 1, apparatus 100 and/or processor 104 may identify one or more constituent visualization components 140 and determine a relationship between them. In some cases, image processing module 144 may classify constituent visualization components 140 to one or more classes, wherein each class may include constituent visualization components 140 having similar relationships. In some cases, each class may include categorizations such as any categorizations as described in this disclosure. In some cases, image processing module 144 may determine an orientation 148 of one or more constituent visualization components 140. For example, image processing module 144 may determine the orientation 148 of a first constituent visualization component 140 within a class and determine the following orientation 148 of constituent visualization components 140 within the class with reference to the first constituent component. In some cases, determining a relationship between one or more constituent visualization components 140 includes determining a spatial distance 152 between two or more constituent visualization components 140 within an image. For example, a particular image may include multiple specimens 124 that are spaced closely or far apart from one another. In some cases, processor 104 may determine a spatial distance 152 in pixels and/or any other unit of measurement between two or more pixels. In some cases, multiple specimens 124 may be located within a single image wherein each specimen 124 may be spaced a distance from one another. In some cases, processor 104 may determine a relationship by determining the spatial distance 152 between one or more specimens 124 within the image.

With continued reference to FIG. 1, apparatus 100 may modify at least one of the one or more constituent visualization components 140. In some cases, modification may include modifying the size of a particular constituent visualization components 140 within an image. In some modification may include the movement of a particular constituent visualization components 140 within an image. For example, a particular constituent visualization component 140 may be located near the bottom of an image wherein apparatus 100 and/or image processing module 144 may move constituent visualization components 140 towards the middle of an image. In some cases, apparatus 100 may identify constituent visualization components 140 using one or more techniques as described in this disclosure. In some cases, image processing module 144 may isolate one or more constituent visualization component 140 as described above. In some cases, the one or more constituent visualization components 140 may be isolated and cropped from image. In some cases, constituent visualization components 140 may be placed on a blank image, such as an image containing a white background or a uniform color background. In some cases, constituent visualization components 140 may be placed equidistant from one another or within particular areas of an image. In one or more embodiments, modifying constituent visualization component 140 may include placing constituent visualization component 140 within the middle or close to the middle of the image. In some cases, modifying constituent visualization components 140 may include isolating constituent visualization components 140 and moving them close together an image. In one or more embodiments, two or more constituent visualization components 140 may be placed relatively far apart from one another, and as a result, a relatively large amount of uninterested space may be separating the constituent visualization components 140. In some cases, image processing module 144 may isolate one or more constituent visualization components 140 and place them closer or farther together based on a predefined configuration set. "Configuration set" for the purposes of this disclosure is a set of information indicating the placement and orientation 148 of one or constituent visualization components 140 within an image. In some cases, configuration set may further include a particular size of an image, the particular orientation 148 of the constituent visualization components 140, and the like. In some cases, the spatial distance 152 may be calculated in reference to one or more constituent visualization component 140. In one or more embodiments, the distance may be calculated in reference to the size of an image. In some cases, processor 104 may be configured to isolate a particular constituent visualization component 140 and fill the area with the surrounding pixel values. For example, a particular section of an isolated constituent visualization components 140 may be filled by pixels having similar color values as the surrounding area. Continuing, a particular area may be filled within an RGB value of (255,255,255) wherein the surrounding values contain a similar pixel color value. In some cases, the original location of constituent visualization component 140 may be filled with one or more predefined values. Such that the original location resembles a corresponding background of Image. In some cases, image processing module 144 may isolate constituent visualization components 140 and transfer the corresponding pixel value to another location on an image. In some cases, constituent visualization components 140 may be moved across an image by changing the location of pixels that correspond to the constituent visualization components 140. For example, a change such as (3,0) may move constituent visualization components 140 in a positive direction along the X axis. Similarly a change such as (−9,12) may move constituent visualization components 140 in a negative direction of 9 pixels along the X axis and the positive direction of 12 pixels along the Y axis.

With continued reference to FIG. 1, modification of one or more constituent visualization components 140 may include the removal of free space within an image. "Free space" for the purposes of this disclosure refers to the section of an image that are not of interest. For example, a particular section of an image that contains no constituent visualization components 140 or portions thereof may be referred to as 'free space'. In some cases, processor 104 may be configured to ensure a particular amount of free space or a range thereof between two or more constituent visualization components 140. In one or more embodiments, wherein a particular row or column of pixels within an image contains only free space, processor 104 may remove the row or column. In some cases, processor 104 may crop one or more area of a particular image that corresponds to free space. In some case, a parameter set as defined above may define a particular amount of free space that may exist between a constituent visualization component 140 and a border of the image and between two constituent visualization components 140. In some cases, processor 104 may remove corresponding free spaces using one or more image processing techniques as described above to conform a particular image to a particular parameter set. In some cases, processor 104 may be configured to use the modified constituent visualization components 140 for further processing. In some cases, modification of constituent visualization components 140 may allow for easier and faster processing wherein images may contain lower pixel counts and as a result, processor 104 may be configured to analyze an image quicker.

With continued reference to FIG. 1, apparatus 100 may modify one or more constituent visualization components 140 as a function of user input 116. In one or more embodiments, a user interface 120 may visualize an image with the identified constituent visualization components 140. In some cases, a user may select a particular constituent visualization component 140 and input a particular location of the constituent visualization components 140. In some cases, user interface 120 may be configured wherein a user may select a particular constituent visualization component 140 through the clicking of a mouse or a button. In some cases, a user may drag a particular constituent visualization component 140 and 'drop' it to a relative location on the image. In some cases, processor 104 may associate the release of the clicking a mouse as a drop. In some cases, the location of the mouse when released may indicate the location of the constituent visualization component 140. In some cases, processor 104 may isolate constituent visualization component 140 and move it to another location as a function of the dragging and dropping. In some cases, a user input 116 may include a keyboard and any other devices as described herein wherein a user may signify to apparatus 100 that a particular constituent visualization component 140 has been selected and a particular location has been inputted for the new location of constituent visualization component 140. In some cases, a user may further crop an image following modification wherein free space surrounding the image may be cropped.

With continued reference to FIG. 1, apparatus 100 may categorize one or more constituent visualization component 140 using an image classifier or any classifier as described herein. In some cases, apparatus 100 may categorize constituent visualization component 140 based on their presence within a particular image, based on their class of specimens 124 as indicated by metadata 132, based on whether the specimen 124 came from the same block and the like. in some cases, one or more constituent visualization components 140 may be categorized to one or more specimen categorization 156. "Specimen categorization" for the purpose of this disclosure is a grouping of related specimens 124. In some cases, specimen categorization 156 may include groupings of related specimens 124 from the same tissue block, grouping of specimens 124 belong to the same class of tissue (e.g. heart, lungs,) grouping of specimens 124 contained within each image and the like. In some cases, a particular specimen categorization 156 may include intra serial sections wherein each specimen 124 within the categorization corresponds to a particular layer of one or more layers retrieved from the tissue block. In some cases, constituent visualization component 140 within a particular specimen categorization 156 may contain similar shapes are they contain sliced layers of a larger tissue block. In some cases, apparatus 100 and/or processor 104 may select one constituent visualization component 140 within each categorization to be selected as a reference constituent visualization component 160. In some cases, each specimen categorization 156 may include layers of a tissue block wherein each layer contains a specimen 124 or constituent visualization component 140. In some cases, two constituent visualization components 140 may contain similar distinctive features such as similar, edges, borders, and points due in situations wherein the two constituent visualization components 140 comprise consecutive layers on a tissue block. In some cases, specimens 124 may be identified as belonging to the same tissue block through metadata 132. "Reference constituent visualization component" is a constituent visualization component 140 that will be referenced (e.g., with respect to size, orientation 148 and the like) in comparison to other constituent visualization components 140, for instance with the same categorization. The reference constituent visualization component 160 may be chosen by selecting the first specimen 124 within a tissue block as indicated by metadata 132. The reference constituent component may additionally or alternatively be chosen based on the presence of the constituent visualization component 140 located on the highest portion of the image. The remaining constituent visualization components 156 within a class or categorization may be referred to as 'remaining constituent visualization components 156. In an embodiment, apparatus 100 and/or processor 104 may categorize constituent visualization components 140 wherein each categorization includes one reference constituent visualization component 160 and one or more remaining constituent visualization components 156. In one or more embodiments, image processing module 144 may receive an orientation 148 of reference constituent visualization component 160 or each reference constituent visualization component 160 within each class or categorization. In some cases, orientation 148 may be determined using key point matching wherein corners, edges, borders and the like may be used to determine a relative orientation 148 of reference constituent visualization component 160. In some cases, the orientation 148 of reference constituent visualization component 160 may be calculated to be at 0. In some cases, orientation 148 of each reference constituent visualization component 160 may be inputted by a user wherein a user may select orientation 148 of the reference constituent visualization component 160. In some cases, processor 104 may determine similarities between two constituent visualization components 140, such as corners edges, borders and the like and determine an orientation 148 of a remaining constituent visualization component 164 in relation to the reference constituent visualization component 160. In one or more embodiments two consecutive layers of a specimen 124 may contain similar corners, edges, borders, any other distinctive features, and the like, wherein processor 104 may receive a reference constituent visualization component 160 and compare it the consecutive constituent visualization component 140 containing similar edges, borders and the like. In some cases, machine vision system as described above may be used to determine the edges, borders and the like of each constituent visualization component 140. In some cases, the consecutive visualization component may be given an orientation 148 relative to reference constituent visualization component 160 based on the orientation 148 of the matched key points. In some cases, consecutive layers within a block may contain similar key points, however nonconsecutive layers may not contain similar key points. In some cases the orientation 148 of consecutive layers of a tissue block may be determined by using the reference constituent visualization component 160 as a reference for the conservative constituent visualization component 140 and using the consecutive constituent visualization component 140 for the next consecutive constituent visualization component 140. For example, a first slide may be considered a reference wherein a second slide in measured is relation to the reference and a third slide is measured in relation to the second slide and an angle is determined in reference to the first slide. As a result, an orientation 148 of each remaining constituent visualization component 164 may be determined based on the previous constituent visualization component 140 that was determined.

With continued reference to FIG. 1, processor may perform one or more image registration techniques such as the one or more image registration techniques as described above in order to determine an orientation of each constituent visualization component 140. Processor 104 may generate a plurality of registrations matching each frame of a plurality of frames (wherein each frame may be correlated to an image) of image data set 128 to a field coordinate system. A "field coordinate system," as used herein is a coordinate system of the field of view, such as a Cartesian coordinate system a polar coordinate system, or the like. In other words, a position of an object within the field coordinate system is static unless the object is moved. Field coordinate system may include a three-dimensional coordinate system. An origin point of field coordinate system may be selected, without limitation, for convenience of calculation, such as selection of a pixel on a frame, such as a first frame as described below which may include without limitation an origin point on a coordinate system of first frame.

With continued reference to FIG. 1, generating plurality of registrations includes defining a first registration of a first frame to the field coordinate system. "Registration" of a frame to a coordinate system, as used in this disclosure, means identifying a location within the coordinate system of each pixel of the frame, either by directly identifying the location of each pixel, and/or by identifying a location of a sufficient number of pixels, such as corner pixels or the like, of the frame to make mathematical determination of location of all other pixels mathematically possible; registration may include identifying coordinates of some excess number of pixels to the minimal number needed to identifying position within the coordinate system, such as identification of one pixel more, twice as many pixels, or ten times as many pixels, where excess pixels may be used to perform error detection and/or correction as described in further detail below. Registration of a frame to field coordinate system may be characterized as a map associating each pixel of a frame, and/or coordinates thereof in a frame coordinate system, to a pixel of field coordinate system. Such mapping may result in a two-dimensional projection of corresponding three-dimensional coordinates on one or more two-dimensional images. First frame may be selected upon initial detection of a vehicle, upon commencement of a predetermined process, based on instructions received from memory 108, and/or that an object of interest is in frame of an image first frame may be selected as a frame generated when such command is received. First frame may include two frames where two frames are captured for stereoscopic images; in this case each such frame may be separately registered, and corresponding subsequent frames may be registered with regard to corresponding original first frame. In the description that follows, it should be assumed that each process described may be performed in parallel on two families or streams of frames forming a stereoscopic image.

With continued reference to FIG. 1, processor 108 may generate an affine motion transformation as a function of the detected changes and calculate a second registration of the second frame to the field coordinate system. An "affine motion transformation," as used in this disclosure, may include any mathematical description usable to describe an affine motion of pixels in a display relative to field coordinate system, where "affine motion" is a motion within a space, such as three-dimensional space, which preserves ratios of lengths of parallel line segments. For instance, and without limitation, affine transformations in three dimensions may be represented by 4×4 matrices. For instance, a translation by a vector [x, y, z] in x, y, and z components of motion according to a Cartesian coordinate system may be represented by the four-by-four matrix:

$$\begin{bmatrix} 1 & 0 & 0 & x \\ 0 & 1 & 0 & y \\ 0 & 0 & 1 & z \\ 0 & 0 & 0 & 1 \end{bmatrix}$$

Rotations in three dimensions can be represented generally by 4×4 matrices as well. For instance, rotations may be represented by multiplying each coordinate set by a matrix computed using Euler angles $\psi$, $\theta$, and $\phi$, representing rotations confined to the yz plane, the zx plane, and the xy plane; these angles may be referred to as roll, yaw, and pitch, respectively. Generally, rotations may be represented by a matrix M, computed as follows:

$$M = \begin{bmatrix} 1 & 0 & 0 \\ 0 & \cos(\psi) & -\sin(\psi) \\ 0 & \sin(\psi) & \cos(\psi) \end{bmatrix} \begin{bmatrix} \cos(\theta) & 0 & \sin(\theta) \\ 0 & 1 & 0 \\ -\sin(\theta) & 0 & \cos(\theta) \end{bmatrix} \begin{bmatrix} \cos(\phi) & -\sin(\phi) & 0 \\ \sin(\phi) & \cos(\phi) & 0 \\ 0 & 0 & 1 \end{bmatrix}$$

Affine transformations may be represented, without limitation, using any alternative or additional mathematical representations and/or processes. Calculation and derivation of linear transformations may be performed, without limitation, using an FPGA, ASIC, or other dedicated hardware module designed to perform rapid arithmetic; trigonometric functions may, as a non-limiting example, be implemented as lookup tables stored, for instance, in read-only memory (ROM) or the like. Alternatively, or additionally, one or more such storage and/or processes may be performed by microprocessors, microcontrollers, or the like, for instance in assembly language or in higher-order languages. Lookup tables, transformation computations, and/or storage of vector and/or matrix values may be performed redundantly, for use in error detection and/or correction, as described in further detail below. Processor 108 may repeat the above-described process to register a plurality of frames and/or each frame of plurality of frames based on registration of first frame.

With continued reference to FIG. 1, processor 104 may reorient the one or more remaining constituent visualization components 164 as a function of the categorization of the constituent visualization component 140 and the orientation 148 of each reference constituent visualization component 160. In some cases, processor 104 may be configured to rotate the remaining constituent visualization component 164 based on orientation 148. In one or more embodiments, the remaining constituent visualization component 164 may be orientated to a '0' degree angle or in relation to the reference constituent visualization component 160. In one or more embodiments, processor 104 may utilize one or more registration transform techniques to rotate the reference constituent visualization components 152 and the remaining constituent visualization components 164. Registration transform techniques may include the matching of one or more key points wherein a constituent visualization component 140 is orientated until is key point is oriented at the same angle as the reference constituent visualization component 160. In some cases, registration transform may include use of one or more transformation matrices wherein a particular constituent visualization component 140 is placed within a matrix and processor 104 converts the matrix into a resulting matrix that takes into account the orientation 148 angle. In some cases, registration transform techniques may include one or more matrix transformation techniques wherein a particular grouping of pixels of a constituent visualization component 140 is transformed using matrix transformation. In some cases, the remaining constituent visualization component 164 may be 'reoriented' wherein 'reoriented' indicates that the reference constituent visualization components 152 and the remaining constituent visualization components 164 are orientated at the same angle.

With continued reference to FIG. 1, processor 104 may generate a configuration set, wherein the configuration set may include any processing techniques as described in this disclosure. For example, configuration set may include the original orientation 148 of each constituent visualization component 140 and the corresponding new orientations 148. Similarly, configuration set may include the particular spatial distance 152 that has been generated between two constituent visualization components 140. In some cases, configuration set may include the particular annotations and/or constituent visualization components 140 that have been removed in an image. In some cases, configuration set may include any modification to the plurality of images and the constituent visualization components 140 as described above.

With continued reference to FIG. 1, processor 104 is configured to generate a plurality of virtual images 168 as a function of image data set 128 and the relationship between the one or more virtual constituent components. "Virtual image" for the purposes of this disclosure is an image that has been modified by apparatus 100. In some cases, each virtual image 168 of the plurality of virtual images 168 may correspond to each image within image data set 128. In one or more embodiments, each image may include constituent visualization component 140 containing only specimens 124 of interest. In some cases, each virtual image 168 may include the removal of one or more constituent visualization components 140 such as annotations, air bubbles, debris, adhesives, and any other unwanted constituent visualization components 140 within one or more images within image data set 128. In some cases, generating one or more virtual images 168 include modifying the location and/or orientation 148 of constituent visualization components 140 and placing the constituent visualization components 140 within particular area of an image. In some cases, virtual image 168 may include a white or uniform colored background wherein each constituent visualization component 140 may be cropped and overlayed on the white background. In one or more embodiments, virtual image 168 may include only constituent visualization components 140 of interest. For example, processor 104 may remove one or more annotations, bubbles and the like that are of no importance to specimen 124. In some cases, virtual image 168 may include constituent visualization components 140 that are spaced equidistant from one another, that are orientated relatively to one another and the like above. In some cases, virtual image 168 may include any modifications made to one or more images using one or more image processing techniques as described above.

With continued reference to FIG. 1, processor 104 may generate a plurality of virtual images 168 using image processing module 144 wherein a particular constituent visualization component 140 is selected and placed within another area of an image. In some cases, processor 104 may generate a virtual image 168 by orienting one or more constituent visualization components 140 within an image as described above. In some cases, processor 104 may generate one or more virtual images 168, through one or more image transformation techniques and/or registration transformation techniques as described above. In some cases, each virtual image 168 may include one or more specimens 124 associated with a particular specimen categorization 156. In some cases, processor 104 may crop constituent visualization components 140 within the same categorization and place them within a single image. In some cases, processor 104 may further orient the constituent visualization components 140 such that the constituent visualization components 140 are all oriented in the same direction.

With continued reference to FIG. 1, in some cases, plurality of virtual images 168 may be generated based on configuration set. In an embodiment, configuration set may include the instructions to generate one or more images. In an embodiment, virtual images 168 may be generated based on configuration set wherein a particular configuration set may indicate how the virtual images 168 may be generated.

With continued reference to FIG. 1, in some cases, processor 104 may determine a spatial distance 152 between one or more constituent visualization components 140 on an image and modify location of the constituent visualization components 140 such that they are equidistant from one another. In some cases, processor 104 may determine a spatial distance 152 between each constituent visualization component 140 as a function of the identification of each constituent visualization component 140 as described above and modify the one or more images such that the constituent visualization components 140 are spaced equally. For example, a first specimen 124 may be spaced equally from a second component and a second component may be spaced equally from a third component. In some cases, a particular location of each constituent visualization component 140 may be spaced equidistant from each border of an image along the X axis. In an embodiment, the outermost edges of each constituent visualization component 140 may be equidistant from the borders on an image along the X axis. In some cases, each constituent visualization component 140 may be viewed as a uniform column, wherein a first constituent visualization component 140 is placed atop a second constituent visualization component 140 and a second constituent visualization component 140 is placed atop a third constituent visualization component 140. In some cases, the one or more constituent visualization component 140 may be placed substantially within the same range along a particular axis. For example, one or more constituent visualization components 140 may be placed substantially within the same region along the Y axis, wherein each constituent visualization component 140 may be viewed from top down. In an embodiment, the particular placement of each constituent visualization component 140 on an image may allow for proper comparison between two or more constituent visualization components 140 located on an image. This may include but is not limited to size comparisons (length and width), color comparisons, comparisons in shape and the like. In some cases, each virtual image 168 may include the reoriented constituent visualization components 140 and their adjusted locations within an image. In some cases each virtual image 168 within plurality of virtual images 168 may be similar in size, wherein the sizing may allow for proper consolidation of one or more images. For example, multiple virtual images 168 may contain similar heights wherein the virtual images 168 may be consolidated to create a larger image (comprising of more than one virtual images 168) with uniform height. similarly, in some cases, multiple virtual images 168 may contain similar dimensions to ensure uniformity between one or more virtual images 168. In some cases, a particular size template may be used to generate each virtual image 168, wherein the size template include information about the length and width of the image. In some cases, each specimen categorization 156 may contain virtual images 168 of similar sizes. In some cases, plurality of virtual images 168 may include images of similar sizing. As discussed above, image processing module 144 may relocate one or more constituent visualization components 140 within an image to ensure that the constituent visualization components 140 are properly located within the resized images.

With continued reference to FIG. 1, each virtual image 168 may include at least one virtual constituent component. "Virtual constituent visualization component" for the purposes of this disclosure is a constituent visualization component 140 that has been modified through one or more modification techniques as described above. For example, virtual constituent visualization component 172 may include a constituent visualization component 140 that has been rotated, a constituent visualization component 140 that has been relocated to another area of an image, and the like. In some cases, constituent visualization component 140 may be partially obstructed by debris, air bubbles and the like. As a result, a virtual constituent visualization component 172 may include a modified constituent visualization component 140 that no longer is obstructed by air bubbles, debris, and the like. In some cases, image processing module 144 may use one or more 'content aware' techniques wherein a particular area desired to be filled, may be filled by surrounding pixels of the area. For example, an annotation or debris on specimen 124 may be removed using image processing module 144, and the resulting area may be filled with the surrounding pixels of the area. In some cases, image processing module 144 may utilize a machine learning model to speculate and/or determine the obstructed sections of a particular constituent visualization component 140. Process and/or image processing module 144 may use a machine learning module, such as a visualization machine learning module for the purposes of this disclosure, to implement one or more algorithms or generate one or more machine-learning models, such as a visualization machine learning model, to generate one or more virtual constituent visualization components 172. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs 116 and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more specimen categorizations 156 corresponding to categories of data elements. As a non-limiting example, training data may include data entered in standardized forms by persons or processes, such that entry of a given data element in a given field in a form may be mapped to one or more categories. Elements in training data may be linked to categories by tags, tokens, or other data elements. A machine learning module, such as visualization machine learning module, may be used to generate visualization machine learning model and/or any other machine learning model described herein using training data. Visualization machine learning model may be trained by correlated inputs and outputs of training data. Training data may be data sets that have already been converted from raw data whether manually, by machine, or any other method. Visualization training data may be stored in database. Visualization training data may also be retrieved from database. In some cases, visualization training data may allow for processor 104 and/or image processing module 144 to compare two data items, to sort efficiently, and/or to improve the accuracy of analytical methods. In some cases, visualization training data may be used to improve the accuracy of generating one or more virtual constituent visualization component 172. In some cases, training data contains classified inputs and classified outputs wherein outputs may contain a higher degree of accuracy by outputting elements with a similar classification.

With continued reference to FIG. 1, in one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from database, such as any database described in this disclosure, or be provided by a user such as a prospective employee, a lab technician, a physician, and/or an employer and the like. In other embodiments, visualization machine-learning module may obtain a training set by querying a communicatively connected database that includes past inputs and outputs. Training data may include inputs from various types of databases, resources, and/or user inputs 116 and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more specimen categorizations 156 corresponding to categories of data elements. As a non-limiting example, training data may include data entered in standardized forms by persons or processes, such that entry of a given data element in a given field in a form may be mapped to one or more of categories. Elements in training data may be linked to categories by tags, tokens, or other data elements.

With continued reference to FIG. 1, visualization training data may include a plurality of specimens 124 and/or a plurality of constituent visualization components 140 correlated to a plurality of virtual constituent visualization component 172. In an embodiment, a particular input may be used to fill an obstructed area of constituent visualization component 140 and generate a virtual constituent visualization component 172. In some cases, training data may indicate that a particular input is correlated to a particular input wherein image processing module 144 may remove the obstruction and fill the area with the correlated output. In one or more embodiments, visualization training data may be created using past inputs correlated to a past outputs. In some cases, visualization training data may include a plurality of specimens 124 that have been input by a user, retrieved from a database and the like. In one or more embodiments, visualization machine learning model may be trained by visualization machine learning model. In one or more embodiments, virtual constituent visualization component 172 may be generated as a function of the machine learning model. In some cases, the machine learning model may be generative wherein portions of constituent visualization component 140 may be filled using one or more generative machine learning techniques as described below. In some cases, training data may be categorized by specimen categorizations 156 wherein each specimen categorization 156 may include inputs and outputs that are classified to the same categorization. In an embodiment, classified training data may improve the accuracy of the machine learning model. In an embodiment, similar looking specimens 124 belonging to differing specimen categorizations 156 may be classified wherein a machine learning model may properly apply the correct correlated outputs.

With continued reference to FIG. 1, in some cases, generating a plurality of virtual images 168 may include receiving an input through user interface 120. In an embodiment, a user may input desired parameters for virtual image 168 wherein virtual image 168 may be generated based on the desired parameters. For example, a user may wish to space each constituent visualization component 140 by a particular distance wherein virtual image 168 may include virtual constituent visualization components 172 that are spaced a particular distance. In some cases, a particular constituent visualization component 140 or a portion thereof may not be identified wherein user input 116 may be used to select a portion of image to be used as constituent visualization component 140. In some cases, a user may select various portions of an image containing unwanted constituent visualization components 140 wherein image processing module 144 may crop and remove the constituent visualization components 140 form the image. For example, debris on the glass slide that has been captured may be removed. In some cases, a user may seek to rotate a particular constituent visualization component 140 such as reference constituent visualization component 160 wherein the remaining constituent visualization components 164 may be rotated relative to the reference. In some cases, a user may wish to keep a particular constituent visualization component 140 wherein user may input through the use interface to keep constituent visualization component 140. In some cases, processor 104 and/or image processing module 144 may generate a particular virtual constituent visualization component 172 wherein a user may seek to view the original constituent visualization component 140 instead. In some cases, a user may input a particular set of images to be viewed consecutively wherein the plurality of virtual images 168 may be generated in a corresponding order. For example, user input 116 may indicate that a particular virtual image 168 should be first in a list of images, and a second virtual image 168 should be second in a list of images. This may allow for proper viewing later on. In some cases, user input 116 may further include the dimensions for each image. For example, a user may input that they would like each image to have a ratio of 8.5×11 similar to a sheet of paper. In another non limiting example, a user may input that each virtual image 168 be of particular format to allow for viewing of multiple virtual images 168 simultaneously on a single display. In some cases, constituent visualization components 140 may include annotations wherein the annotations may include writing, portions, thereof or any other markings or indication made by an individual. In some cases, processor 104 may be configured to receive one or more configurable parameters 176 wherein the configurable parameters 176 include instruction on how particular virtual images 168 should be created. For example, configurable parameters 176 may include any user input 116 as described above, such as user input 116 relating to the rotation of a constituent visualization component 140. In some cases, each element of configuration set may include a configurable parameter 176, wherein a plurality of configurable parameters 176 may make up a particular configuration set. In some cases, configurable parameters 176 may include inputs by the user to keep or remove particular annotations on an image. For example, a particular annotation may partially obstruct a particular constituent visualization component 140. In some cases, processor 104 and/or image processing module 144 may be automatically configured to remove the annotations absent user input 116. In some cases, the configurable parameters 176 may indicate to keep a particular annotation on the constituent visualization component 140 wherein the virtual constituent visualization component 172 contains the annotation as well. In some cases, the annotation may be viewed as part of the constituent visualization component 140 wherein rotation of the constituent visualization component 140 will rotate the annotation as well. In some cases, processor 104 and/or image processing module 144 may be configured to remove the one or remove annotations based on the one or more configurable parameters 176. For example, if a particular configurable parameter 176 indicates that an annotation should stay then image processing module 144 and/or processor 104 may leave the annotation within the image. In some cases one or more configurable parameters 176 may be received as a function of user input 116. In some cases, processor 104 may receive one or more configurable parameters 176 from a database or a storage.

With continued reference to FIG. 1, in some cases, configuration set as described above may be presented to a user wherein a user may modify configuration set, wherein modification of configuration set may cause modification of virtual images 168. For example, modification of a particular orientation 148 within configuration set may cause orientation 148 of a particular constituent visualization component 140 within one or more virtual images 168. In an embodiment, a particular configuration set may be presented to a user prior to generation of one or more images wherein the virtual images 168 may be generated after acceptance or modification of the configuration set. In some cases, a user may modify configuration set wherein the plurality of virtual images 168 are generated as a function of the modification. In some cases, configuration set may include information associated with each image within image data set 128 and the associated configurations and/or configurable parameters 176 of the particular image.

With continued reference to FIG. 1, in some cases, images within image data set 128 may include images having lower pixel density and/or quality. In some cases, images with lower pixel density may allow for quicker processing of each image. In some cases, images with lower pixel density and/or lower size may allow for quicker processing of each image within image data set 128. In some cases, processor 104 and/or processing module may generate configuration set wherein configuration set may be used on associated higher images to allow for quicker processing. In some cases, each image within image data set 128 may be associated with a similar image of higher quality. In some cases, processor 104 may generate configuration set based on image data set 128 and generate virtual images 168 based on the images of higher quality using configuration set. In some cases, configuration set may include registration transforms and other information associated with orientation 148 of the constituent visualization components 140 wherein processor 104 may be configured to apply configuration set to the higher quality images. In some cases, processor 104 may use a pyramid processing technique. "Pyramid processing" includes the processing of a lower resolution image to obtain a particular set of results, wherein the results may be applied to a higher resolution image. In some cases, processor 104 may make one or more determinations and/or calculations as described in this disclosure on the images within image data set 128 and store the results as configuration set. Configuration set may then be used to make one or more determinations and/or modifications to higher resolution photos containing the same images. In some cases, processor 104 may 'up sample' the results such that the results may be applied to a higher resolution image. Up sampling is a process in which a particular calculation or signal is expanded and applied to a higher signal. For example, an image may be up sampled such that it now contains a higher resolution. The image may be up sampled through the addition of pixels to the image through one or more interpolation techniques. In some cases, calculations made on lower resolution images may be up sampled such that they may be applied to higher resolution images. In some cases, a particular signal or calculation may be expanded by a factor of 2. In situations where the higher signal is larger by a factor of two. With respect to images, calculations performed on lower resolution images may be up sampled with respect to the difference in ratio between the smaller image and the larger image. In some cases, configuration set may be up sampled using one or more up sampling techniques such as bilinear interpolation, bicubic interpolation and the like. In some cases, processor may be configured to receive classified portions of each image within image data set and apply the classified portions to the higher image. In some cases, processor may be configured to receive a bounding box of each classified portion of an image and using the bounding box, identify one or more constituent visualization components in the higher resolution image. In some cases, configuration set may include the bounding box wherein the bounding box include a point of reference for object detection. In some cases, processor may be configured to calculate a ratio between the smaller image within image data set 128 and the higher resolution to perform proper up sampling of the calculations within configuration set. In some cases, processor may be configured to perform one or more image registration processes as described in this disclosure wherein various features, such as edges, borders and the like are analyzed, and apply those processes to the higher resolution image. In some cases, configuration set may be configured to receive the parameters that describe the relationship between the reference constituent component 160 and the remaining constituent components 164 and apply them to the higher resolution image using one or more upsampling methods.

With continued reference to FIG. 1, processor 104 may receive a plurality of high-resolution images wherein each high resolution is associated with an image from image data set 128. In some cases, the plurality of high-resolution images may be captured using a macro camera 136, an automated microscope, an imaging device, a high-resolution imaging device and other devices as described in this disclosure. In some cases, processor 104 may use configuration set to modify one or more high resolution images to generate one or more virtual images 168. In an embodiment, a particular virtual image 168 may include a high resolution that has been modified based on the configuration set that has been generated. In an embodiment, each high-resolution image is associated with a particular image within image data set 128 wherein the configurable parameters 176 for the image within image data set 128 may be transferred to the high-resolution image. In some cases, generation of configuration set may allow for modification of high-resolution images with quicker processing times. In an embodiment, a particular image having lower pixel density may be processed quicker than an image with higher pixel density. In an embodiment, processor 104 may use image processing module 144 to detect key points within the high-resolution image and compare those key points to the low-resolution image. In an embodiment, processor 104 may then use configuration parameters to modify one or more constituent visualization component 140 within image data set 128. In some cases, constituent visualization components 140 within the high-resolution images may be reoriented based on configuration set or based on the reorienting of the images within image data set 128 as described above. In some cases, any modifications described above and/or any modification as described within configuration set may be used to modify one or more high resolution images.

With continued reference to FIG. 1, processor 104 is configured to generate a consolidated virtual image 180 as a function of the plurality of virtual images 168. In some cases, consolidated virtual image 180 may further be generated as a function of image data set 128. "Consolidated virtual image 180" for the purposes of this disclosure is a processed image composed of multiple images. In some cases, consolidated virtual image 180 may include an image of multiple virtual images 168 stitched together. For example, a first virtual image 168 and a second virtual image 168 may be stitched together to create one larger image. In some cases, generating consolidated virtual image 180 may include matching an edge of a first virtual image 168 and a second virtual image 168 together through one or more commonly known stitching techniques used on one or more computing devices. In some cases, consolidated virtual image 180 may include one or more images that have been stitched together wherein a border of a first image may be connected to a border of a second image. In some cases, processor 104 may use one or more positioning techniques to overlay one or more images together. In some cases, each virtual image 168 may include a similar height wherein consolidated virtual image 180 contains a uninform height. In some cases each virtual image 168 may further include a uniform length wherein the length of consolidated image may be composed of 4 images of equal length. In some cases, each image within consolidated image may be separated by a border. In some cases, consolidated image may be composed of a template wherein each virtual image 168 may be positioned within the template. In some cases, processor 104 may be configured to retrieve one or more templates from a database wherein a particular template may be used to generate one or more consolidated images. In some cases, each consolidated image may include more than one virtual image 168 that were captured in sequence, such as images captured after one another as indicated by metadata 132 within image data set 128. In some cases, each consolidated image may include more than one virtual image 168 belonging to a particular categorization such as a specimen categorization 156. In some cases, each consolidated image may include virtual images 168 that are associated with image captured from the same stack. In an embodiment, consolidated image may allow for ergonomic viewing wherein multiple specimens 124 may be viewed simultaneously. In an embodiment, consolidated virtual image 180 may allow for ergonomic viewing wherein each virtual image 168 is aligned and allows for proper arrangement of one or more specimens 124 within the image. In some cases, processor 104 may use one or more image stitching techniques to create a consolidated virtual image 180. In some cases, processor 104 may receive a particular image template wherein the image template is configured to receive one or more virtual images 168 having particular size requirements. In some cases, each virtual image 168 may be of uniform size, wherein a particular template may be configured to receive a particular image. In some cases, each template may be configured to receive virtual image 168. In some cases, each image template may include one or more sections wherein each section may be configured to receive a particular image. In some cases, generating consolidated image may include receiving the high-resolution images such as images retrieved from a macro camera 136 wherein the consolidated image may be composed of more than one macro images. In some cases, processor 104 may be configured to generate a consolidated macro image wherein the consolidated macro image may be consistent with a consolidated virtual image 180, however the images within consolidated macro image may be composed of macro images and/or high-quality images. In some cases, processor 104 is further configured to display consolidated virtual image 180 to a user using one or more displays and/or display devices as described in this disclosure.

Figure 2B:
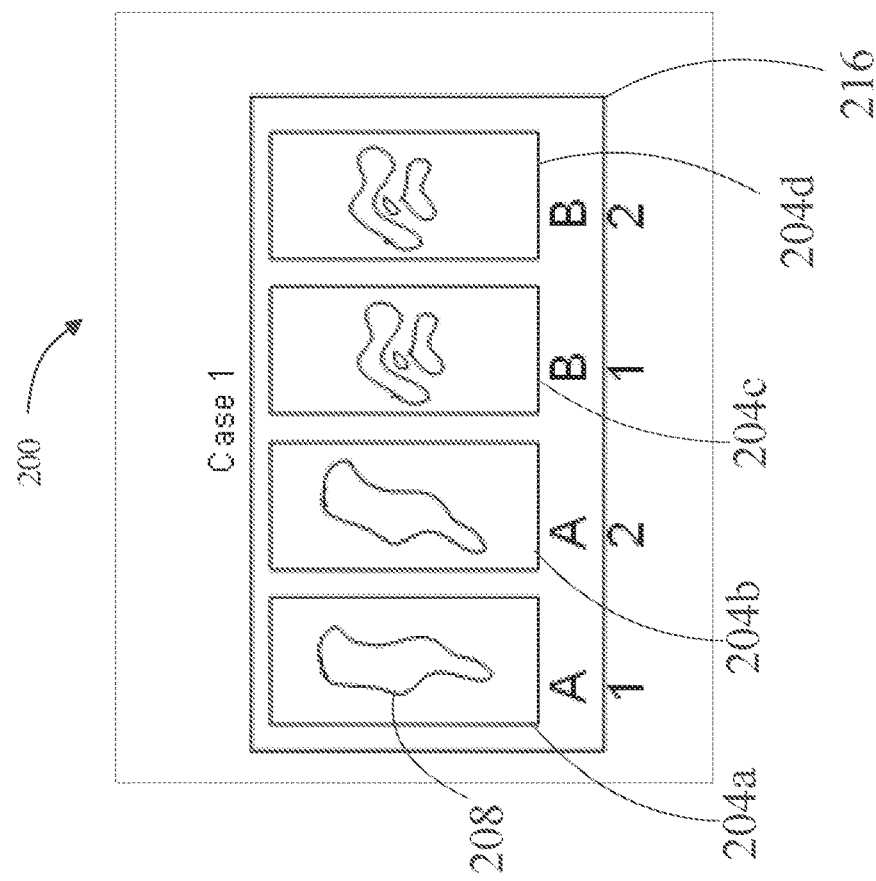
FIGS. 2A-B are exemplary diagrams of one or more processes of the apparatus as described with respect to FIG. 1.
Figure 2A:
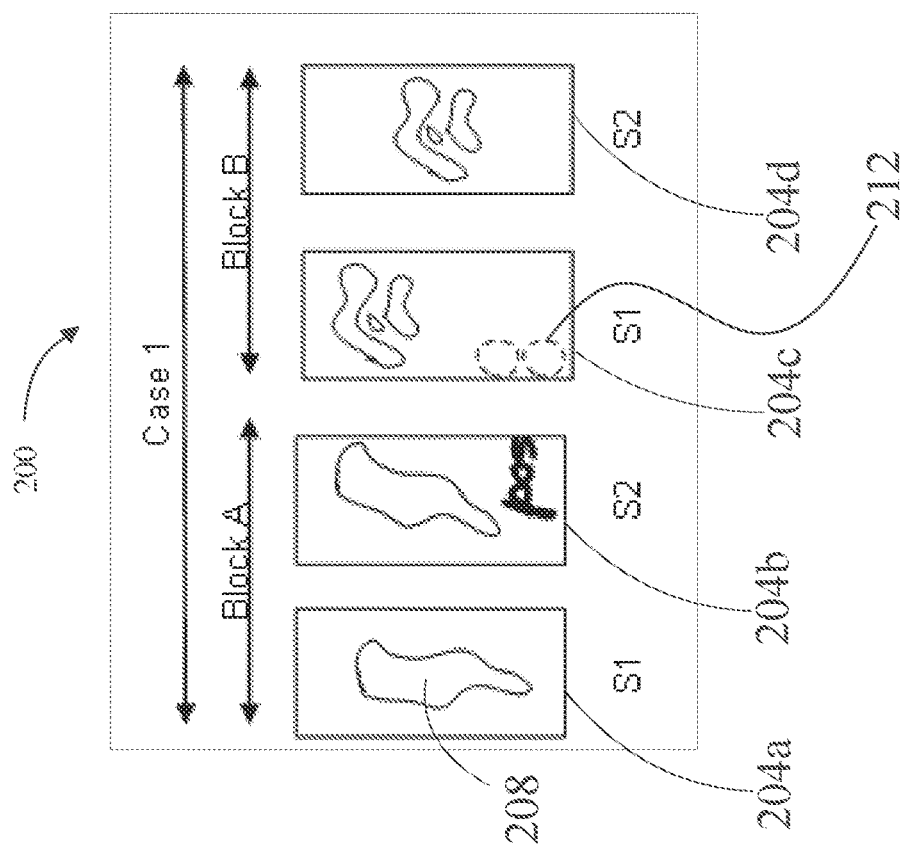

Referring now to FIGS. 2A-B, various diagrammatic representations of one or more processes of generating a consolidated virtual image as described above is illustrated. Referring to FIG. 2A, representation 200*a* depicts multiple images 204*a-d* wherein each image 204*a-d* may include an image of specimen 208. In some cases, each image 204*a-d* may include a particular specimen 208*a* belonging to a particular tissue block or to a particular categorization. In some cases, each image may contain specimens 208 located on a particular area of the image 204a-d. In some cases, each image 204a04 may be of varying size wherein a first image may be larger in height than a second image. In some cases, two specimens 208 within one or more images 204a-d may belong to the same categorization. In some cases, each image 204a-d may contain one or more annotations 212, wherein the annotations 212 may be composed of wording, air bubbles, and the like as described above. In some cases, diagrammatic representation 220a may depict one or more images on a device display.

Referring now to FIG. 2B, diagrammatic representation may depict one or more images 204a-d, wherein each image may have been modified. In some cases, the images may be uniform in height in comparison to one another. In some cases, the images 204a-d may be uniform in size in comparison to one another. In some cases, each image 204a-d, may contain specimen 208 wherein specimen may be located substantially within a middle of each image 204a-d. In some cases, one or more processes as described in reference to FIG. 1, may allow for transformation of one or images 204a-d to ensure that each image is of proper size. In some cases, one or more processes as described above may allow for modification of specimen 208 wherein specimen may be moved and/or rotated from one section of another on image. In some cases, annotations 212 within each image 204a-d may be removed wherein only specimen 208 is present. In some cases, images 204a-d may be consolidated in consolidated image 216. Consolidated image 216 may include one or more specimens relating to the same case, category, tissue block and the like. In some cases, consolidated image may be generated using any processes as described above in reference to FIG. 1.

Figure 3B:
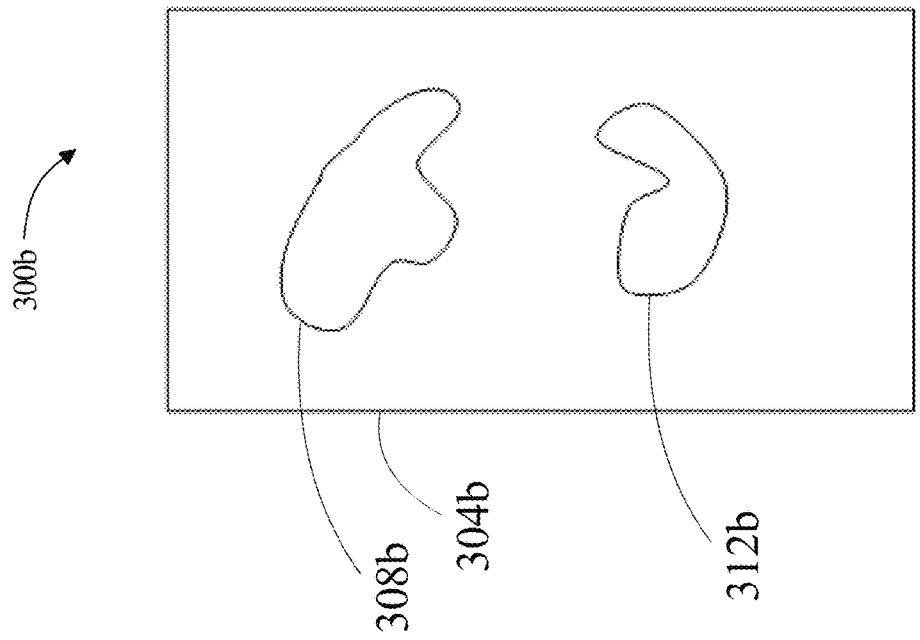
FIGS. 3A-B are exemplary embodiments of images and corresponding virtual images that have been modified through one or more processes as described with respect to FIG. 1.
Figure 3A:
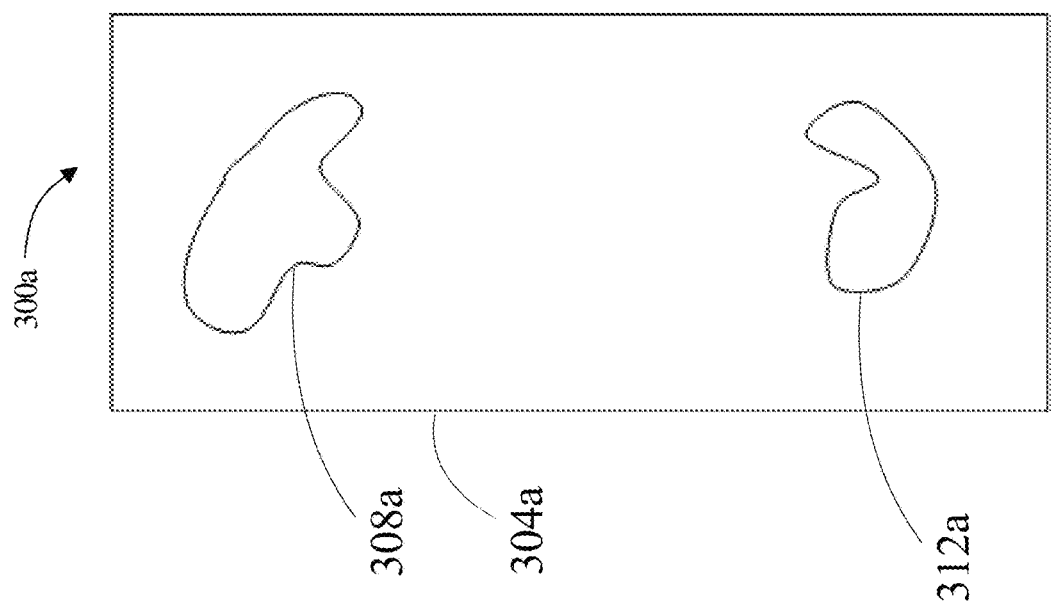

Referring now to FIG. 3A, an exemplary image 300a of a glass slide 304a is illustrated. In some cases, glass slide may include a first specimen 308a and a second specimen 308b. In some cases, image 300a may be consistent with an image within image data set as described above. In some cases, class slide 304a may contain a plurality of free space wherein first specimen 308a and second specimen 312a are separated by some spatial distance. In an embodiment, a user may seek to view each specimen in closer relation to one another. In one or more embodiments, a user may seek to remove any unwanted free space between the two specimens. In some each first specimen 308a and second specimen may be consistent with constituent visualization components as described above.

Referring now to FIG. 3B, an exemplary virtual image 300b of image 300a is illustrated. In some cases, virtual image 300b contains a modified image 300a. In some cases, one or more processes as described above may move one or more specimens on the virtual glass slide 304b. in some cases, virtual glass slide may be a modified glass slide 304a wherein a portion of glass slide 304a is removed. In some cases, first virtual specimen 308b may be moved in relation to first specimen 308a and second virtual specimen 312b may be moved in relation to second specimen 312a. IN an embodiment, virtual image 300b Includes one or more modifications to image 300a as described above.

Referring now to FIG. 4A, an exemplary image 400a of a glass slide containing a first specimen 408a, a second specimen 412a, and a third specimen 416a. In some cases, all the specimens 408a, 412a, 416a may originate from the same tissue block. In some cases, the specimens may represent consecutive layers of a tissue block wherein the specimens may contain similar shapes. In some cases, second specimen 412a and third specimen 416a may be oriented differently from first specimen 408a within image 400a.

Referring now to FIG. 4B, virtual image 400b may include modified image 400a, in some cases virtual image 400b may be provide for proper spatial distance between one or more specimens on virtual glass slide 404b. In some cases, apparatus may generate virtual image 400b wherein first virtual specimen 408b, second virtual specimen 412b and third virtual specimen 416b are all oriented relatively to one another. Similar to FIG. 3B, virtual glass slide 404b may be smaller than glass slide 404a wherein any empty or unneeded space may be removed.

Figure 5B:
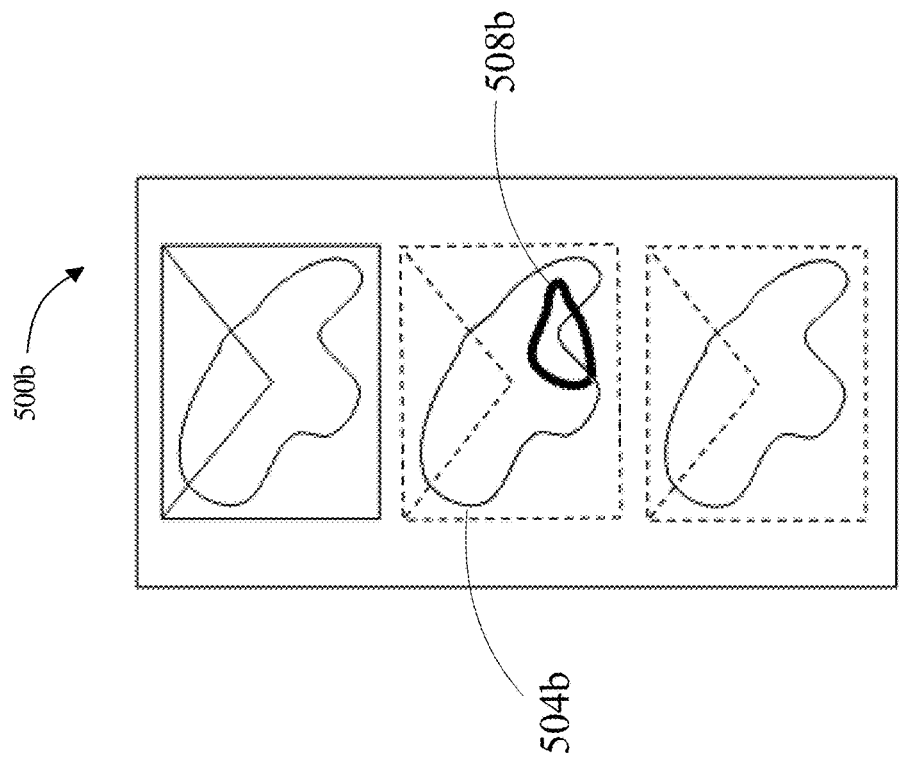
FIGS. 5A-B are yet another exemplary embodiment of images and corresponding virtual images that have been modified through one or more processes as described with respect to FIG. 1.
Figure 5A:
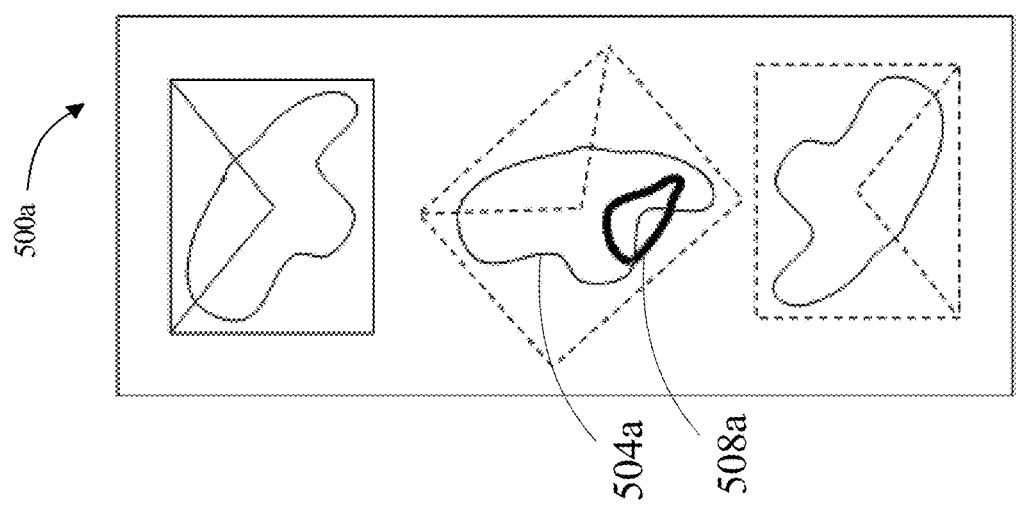

Referring now to FIGS. 5A-B in some cases, image 500a may contain a specimen 504a having an annotation 508a. In some cases, virtual image 500b may keep the annotation 508b based on user input. For example, a user may input that they wish for the annotation 508a-b to stay on top of specimen 504a wherein virtual specimen 504b may contain annotations as well. In some cases, annotation 508a may be removed based on user input.

Figure 6:
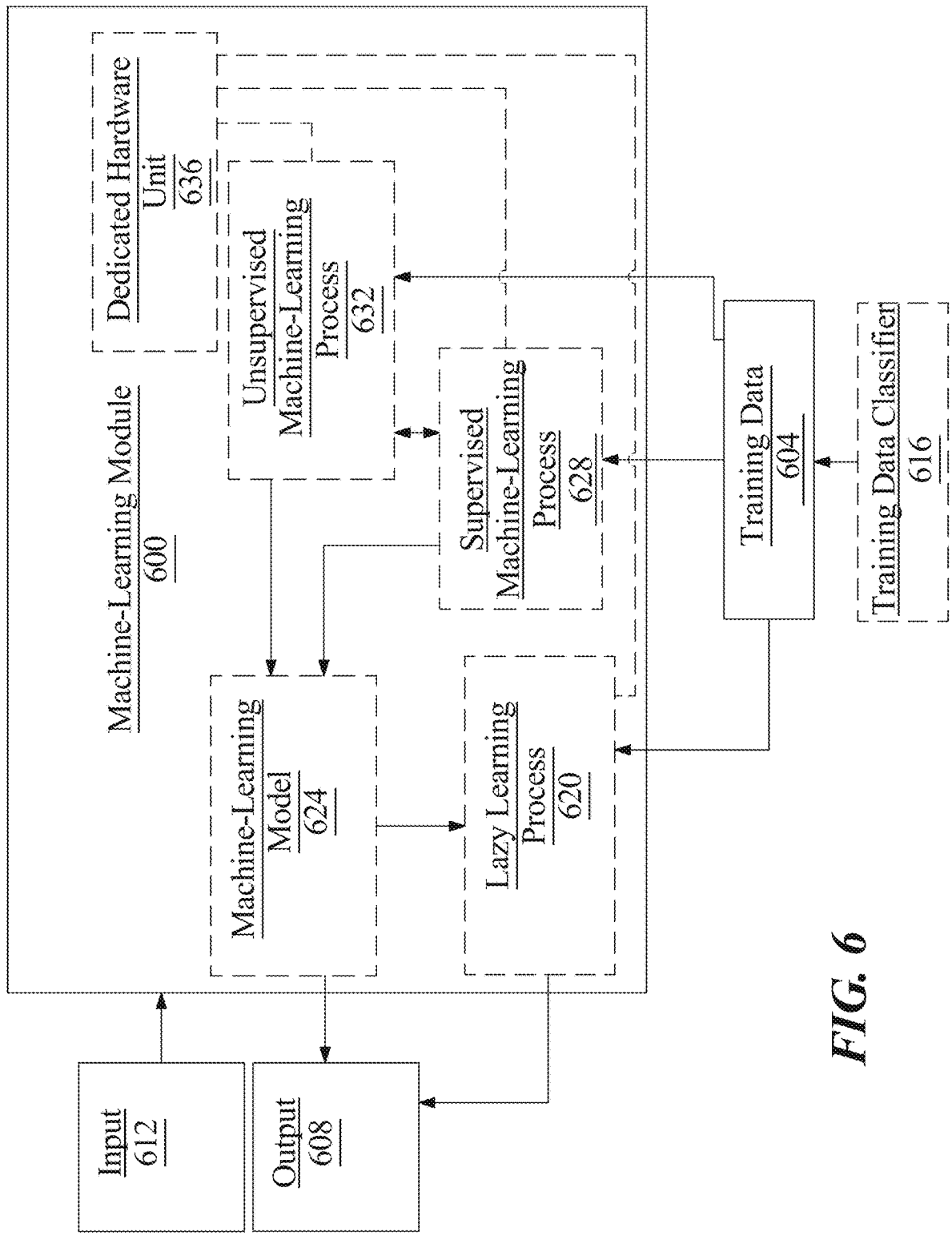
FIG. 6 is a block diagram of exemplary embodiment of a machine learning module.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm instantiated in hardware or software logic, data structures, and/or functions that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example inputs may include images of specimens within image data set as described above and outputs may include virtual images of specimens as described above.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to classes such as, for example, specimen categorization. In some cases, a particular specimen may originate from heart tissue whereas another specimen may originate from lung tissue. In an embodiment, classifying inputs and outputs to one or more specimen categorizations may allow for proper identification of a particular specimen. Similarly, in instances where two specimens relating to differing categorizations may have similar qualities classification may allow for proper selection of an output. In an embodiments, only virtual images associated with the same categorization of specimens as input may be chosen.

With further reference to FIG. 6, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 6, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 6, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 6, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 6, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include image data set as described above as inputs, virtual images as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

With further reference to FIG. 6, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 6, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 632 may not require a response variable; unsupervised processes 632 may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 6, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 6, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 6, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 6, one or more processes or algorithms described above may be performed by at least a dedicated hardware unit 636. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 636 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 636 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 636 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 7:
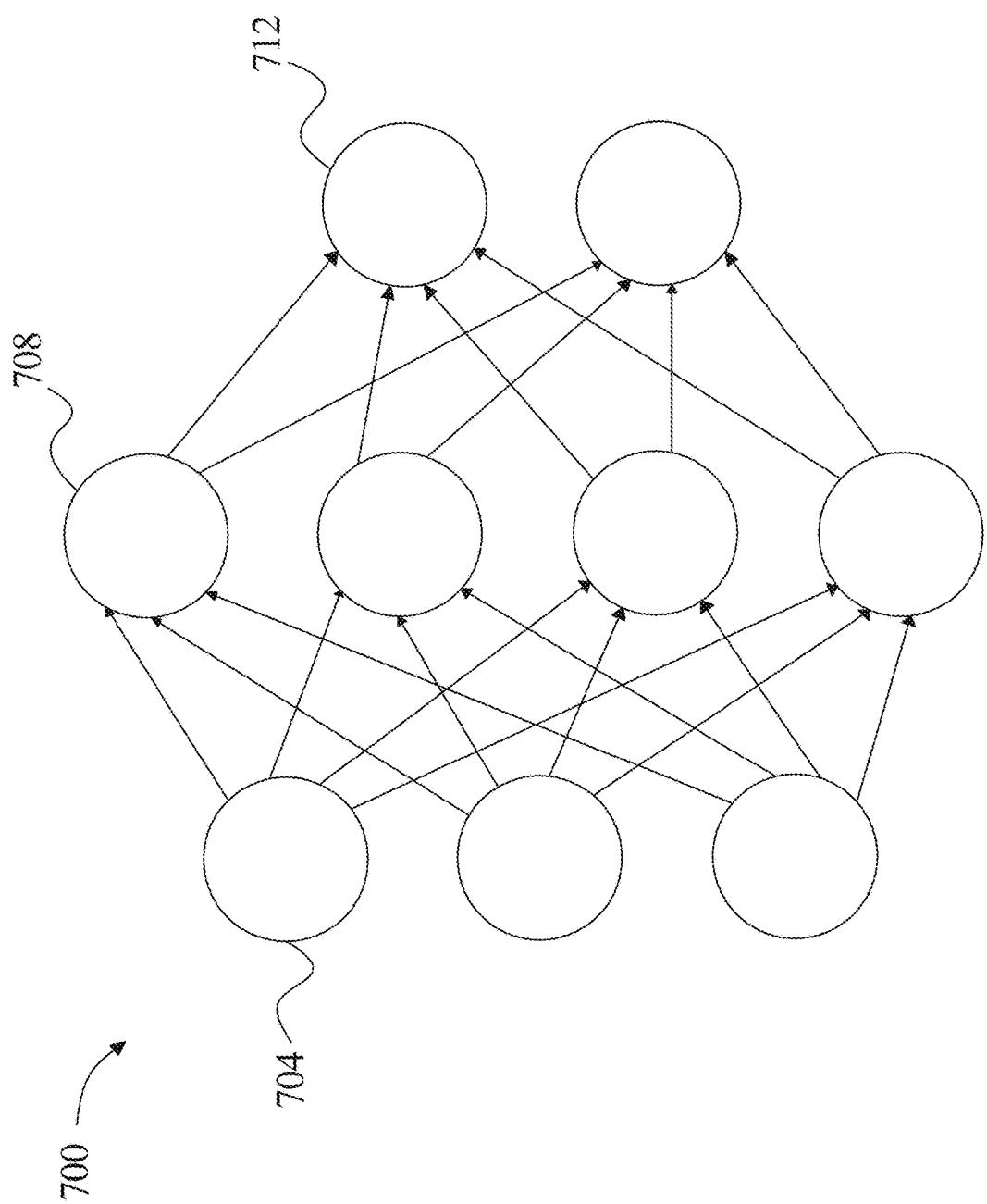
FIG. 7 is a diagram of an exemplary embodiment of a neural network.

Referring now to FIG. 7, an exemplary embodiment of neural network 700 is illustrated. A neural network 700 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 8:
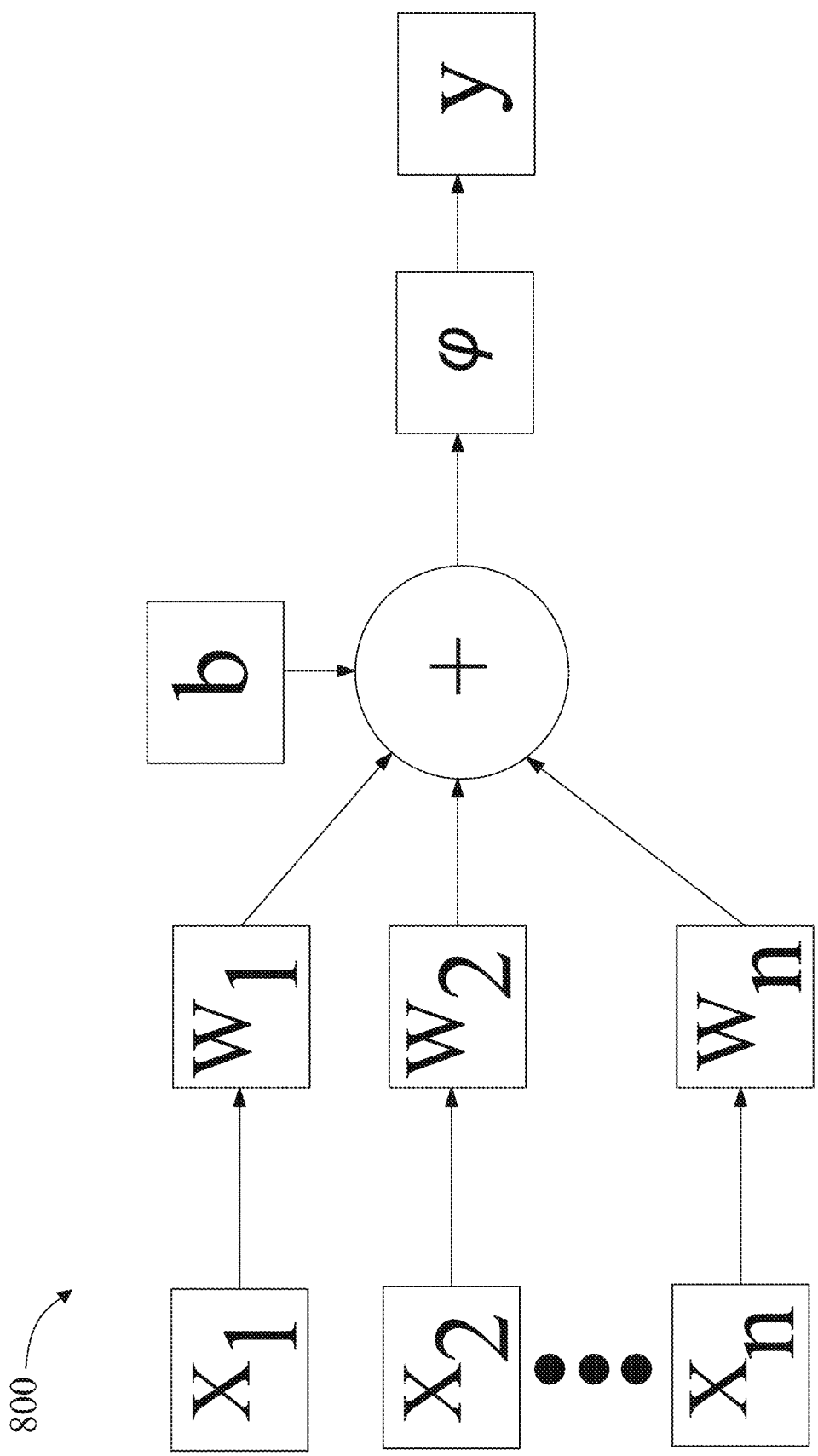
FIG. 8 is a block diagram of an exemplary embodiment of a node of a neural network.

Referring now to FIG. 8, an exemplary embodiment of a node 800 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(2/\pi(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 9:
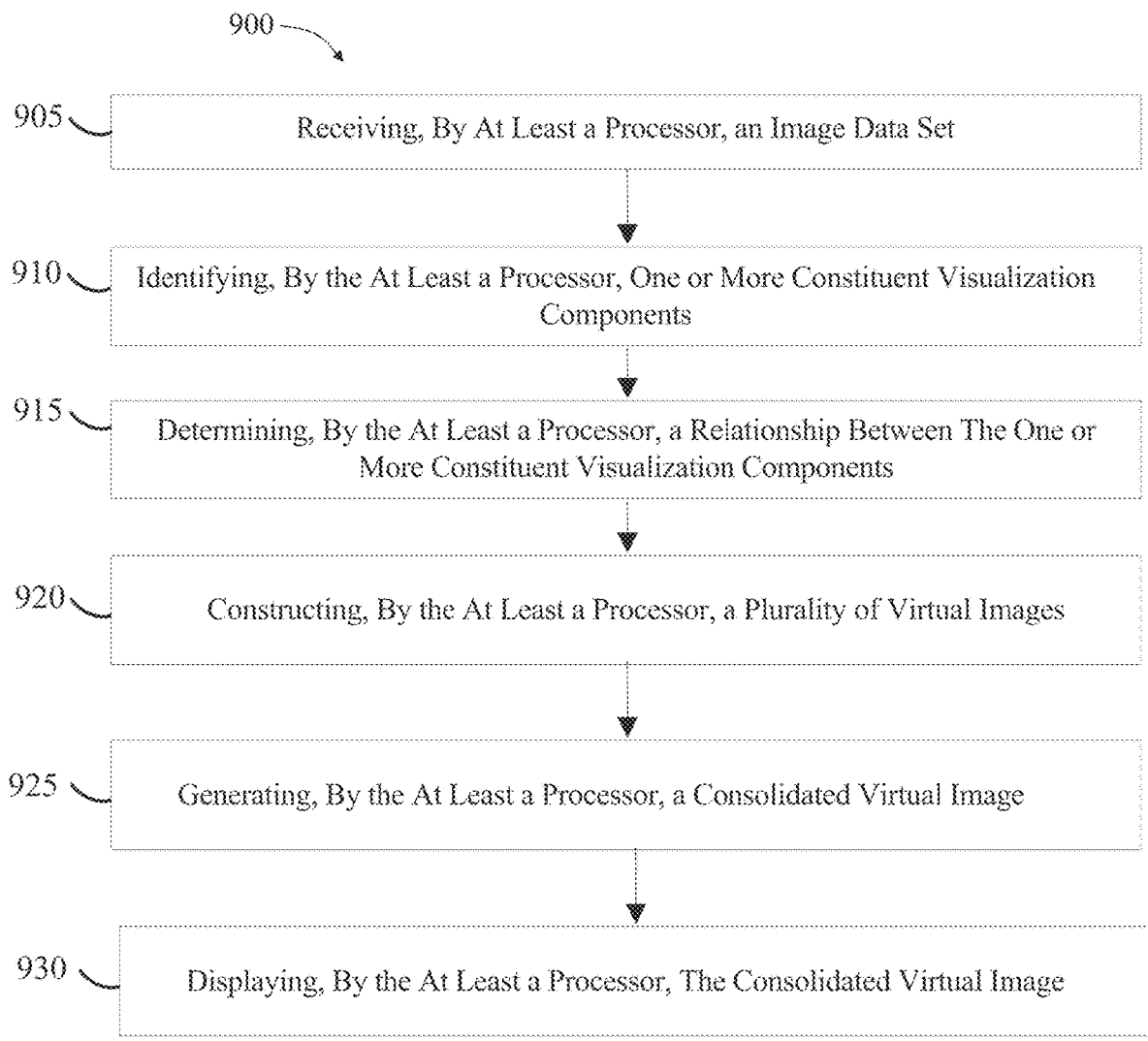
FIG. 9 is a flow diagram illustrating an exemplary embodiment of a method for visualization of digitized glass slides.

Referring now to FIG. 9, method 900 for visualization of digitized class slides belonging to a patient case is desired. At step, 905 method 900 includes receiving, by at least a processor, an image data set having a plurality of images of one or more specimen and metadata of the plurality of images of the one or more specimen. In some cases, receiving, by the at least a processor, the image data set includes acquiring at least one macro image of the specimen through a macro camera. This may be implemented with reference to FIGS. 1-8 and without limitation.

With continued reference to FIG. 9, at step 910, method 900 includes identifying, by the at least a processor, one or more constituent visualization Components for each image of the plurality of images within image data set. In some cases, method 900 may further include determining, by the at least a processor, for each image of the plurality of images within image data set, the membership of a set of images for visualization as a function of image data set. This may be implemented with reference to FIGS. 1-8 and without limitation.

With continued reference to FIG. 9, at step 915, method 900 includes determining, by the at least a processor, a relationship between one or more constituent visualization components as a function of the image data set. In some cases, determining, by the at least a processor, a relationship between the one or more constituent visualization components includes identifying the one or more constituent visualization components, modifying at least one of the one or more constituent visualization components, and determining the relationship between the one or more constituent visualization components as a function of the modification. In some cases, determining, by the at least a processor, a relationship between one or more constituent visualization components further includes categorizing the one or more constituent visualization components into one or more specimen categorizations, wherein each specimen categorization includes a reference constituent visualization component and one or more remaining constituent visualization components, receiving an orientation of each reference constituent visualization components and the one or more remaining constituent visualization components of the on one or more specimen categorizations and reorienting the one or more remaining constituent visualization components as a function of the categorization and the orientation of each reference constituent visualization components of the one or more reference constituent visualization components. In some cases, determining, by at least a processor, a relationship between one or more constituent visualization components includes identifying one or more constituent visualization components using an image processing module. This may be implemented with reference to FIGS. 1-8 and without limitation.

With continued reference to FIG. 9, at step 920, method 900 includes constructing, by the at least a processor, a plurality of virtual images as a function of the image data set and the relationship between the one or more virtual constituent components, wherein each of plurality of the images includes at least one virtual constituent component. In some cases, constructing, by the at least a processor, the plurality of virtual images as a function of the image data set and the relationship between the one or more virtual consistent components further includes, receiving an input through the user interface, and generating the plurality of virtual images as a function of the input. In some cases, constructing, by the at least a processor, the plurality of virtual images as a function of the image data set and the relationship between the one or more virtual constituent components further includes generating a plurality of virtual images as a function of the reorienting of the one or more constituent visualization components. In some cases, constructing, by the at least a processor, the plurality of virtual images further includes receiving a plurality of high-resolution images, wherein each image of the plurality of high-resolution images is associated with each image of the image data set and generating a plurality of virtual images as a function of the plurality of high-resolution images and the reorienting of the one or more remaining constituent visualization components. In some cases, constructing, by the at least a processor, the plurality of virtual images as a function of the image dataset further includes determining a spatial distance between each reference constituent visualization and the one or more remaining virtual constituent components for each image of the plurality of images and constructing at least one virtual image of the plurality of virtual images as a function of the spatial distance. In some cases, constructing, by the at least a processor, a plurality of virtual images as a function of the image dataset further includes identifying one or more annotations on at least one image of the plurality of images, receiving one or more configurable parameters of the plurality of images, and removing the one or more annotations as a function of the one or more configurable parameters. Ins some cases, the one or more configurable parameters are received as a function of user input. This may be implemented with reference to FIGS. 1-8 and without limitation.

With continued reference to FIG. 9, at step 925 method 900 includes generating, by the at least a processor, a consolidated virtual image as a function of the plurality of virtual images. in some cases, generating a consolidated virtual image as function of the plurality of virtual images includes generating a consolidated macro image as a function of the plurality of virtual images. This may be implemented with reference to FIGS. 1-8 and without limitation.

With continued reference to FIG. 9, at step 930, method 900 includes displaying, by the at least a processor, the consolidated virtual image. This may be implemented with reference to FIGS. 1-8 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIRE-WIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for visualization of digitized slides belonging to a patient case comprising:
   a processor; and
   a memory communicatively connected to the processor, the memory containing instructions configuring the processor to:
     receive an image data set comprising a plurality of images of one or more specimens and metadata of the plurality of images of the one or more specimens;
     identifying one or more constituent visualization components for each image of the plurality of images within image data set;
     determine a relationship between the one or more constituent visualization components as a function of the image data set, wherein determining the relationship between the one or more constituent visualization components further comprises:
       categorizing the one or more constituent visualization components into one or more specimen categorizations, wherein each specimen categorization comprises a reference constituent visualization component and one or more remaining constituent visualization components;
       receiving an orientation of each reference constituent visualization components and the one or more remaining constituent visualization components of the one or more specimen categorizations; and
       reorienting the one or more remaining constituent visualization components as a function of the categorization and the orientation of each reference constituent visualization components of the one or more reference constituent visualization components;
     construct a plurality of virtual images as a function of the image data set and the relationship between the one or more constituent visualization components, wherein each virtual image of the plurality of virtual images comprises at least one virtual constituent component;
     generate a consolidated virtual image as a function of the plurality of virtual images; and
     display the consolidated virtual image.

2. The apparatus of claim 1, wherein constructing the plurality of virtual images as a function of the image data set and the relationship between the one or more virtual constituent components further comprises:
   receiving an input through a user interface; and
   generating the plurality of virtual images as a function of the input.

3. The apparatus of claim 1, wherein determining a relationship between the one or more constituent visualization components comprises:
   modifying at least one of the one or more constituent visualization components; and
   determining the relationship between the one or more constituent visualization components as a function of the modification.

4. The apparatus of claim 1, wherein:
   receiving the image data set comprises acquiring at least one macro image of the specimen using a macro camera;
   constructing the plurality of virtual images as a function of the image data set and the relationship between the one or more virtual constituent components further comprises:
      generating a plurality of virtual images as a function of the reorienting of the one or more constituent visualization components; and
   generating a consolidated virtual image as function of the plurality of virtual images comprises generating a consolidated macro image as a function of the plurality of virtual images.

5. The apparatus of claim 1, wherein constructing the plurality of virtual images further comprises:
   receiving a plurality of high-resolution images, wherein each image of the plurality of high-resolution images is associated with each image of the image data set; and
   generating a plurality of virtual images as a function of the plurality of high-resolution images and the reorienting of the one or more remaining constituent visualization components.

6. The apparatus of claim 1, wherein constructing the plurality of virtual images as a function of the image data set further comprises:
   determining a spatial distance between each reference constituent visualization and one or more remaining virtual constituent components for each image of the plurality of images; and
   constructing at least one virtual image of the plurality of virtual images as a function of the spatial distance.

7. The apparatus of claim 1, wherein constructing a plurality of virtual images as a function of the image data set further comprises:
   identifying one or more annotations on at least one image of the plurality of images;
   receiving one or more configurable parameters of the plurality of images; and
   removing the one or more annotations as a function of the one or more configurable parameters.

8. The apparatus of claim 7, wherein the one or more configurable parameters are received as a function of user input.

9. The apparatus of claim 1, wherein determining a relationship between one or more constituent visualization components comprises identifying one or more constituent visualization components using an image processing module.

10. A method for visualization of digitized slides belonging to a patient case, the method comprising:
    receiving, by at least a processor, an image data set comprising a plurality of images of one or more specimen and metadata of the plurality of images of the one or more specimen;
    identifying, by the at least a processor, one or more constituent visualization components for each image of the plurality of images within image data set;
    determining, by the at least a processor, a relationship between the one or more constituent visualization components as a function of the image data set, wherein determining the relationship between the one or more constituent visualization components further comprises:
       categorizing the one or more constituent visualization components into one or more specimen categorizations, wherein each specimen categorization comprises a reference constituent visualization component and one or more remaining constituent visualization components;
       receiving an orientation of each reference constituent visualization components and the one or more remaining constituent visualization components of the one or more specimen categorizations; and
       reorienting the one or more remaining constituent visualization components as a function of the categorization and the orientation of each reference constituent visualization components of the one or more reference constituent visualization components;
    constructing, by the at least a processor, a plurality of virtual images as a function of the image data set and the relationship between the one or more constituent visualization components, wherein each virtual image of the plurality of the images comprises at least one virtual constituent component;
    generating, by the at least a processor, a consolidated virtual image as a function of the plurality of virtual images; and
    displaying, by the at least a processor, the consolidated virtual image.

11. The method of claim 10, wherein constructing, by the at least a processor, the plurality of virtual images as a function of the image data set and the relationship between the one or more virtual constituent components further comprises:
    receiving an input through a user interface; and
    generating the plurality of virtual images as a function of the input.

12. The method of claim 10, wherein determining, by the at least a processor, a relationship between the one or more constituent visualization components comprises:
    modifying at least one of the one or more constituent visualization components; and
    determining the relationship between the one or more constituent visualization components as a function of the modification.

13. The method of claim 10, wherein:
    receiving, by the at least a processor, the image data set comprises acquiring at least one macro image of the specimen using a macro camera;
    constructing, by the at least a processor, the plurality of virtual images as a function of the image data set and the relationship between the one or more virtual constituent components further comprises:
       generating a plurality of virtual images as a function of the reorienting of the one or more constituent visualization components; and
    generating a consolidated virtual image as function of the plurality of virtual images comprises generating a consolidated macro image as a function of the plurality of virtual images.

14. The method of claim 10, wherein constructing, by the at least a processor, the plurality of virtual images further comprises:

receiving a plurality of high-resolution images, wherein each image of the plurality of high-resolution images is associated with each image of the image data set; and generating a plurality of virtual images as a function of the plurality of high-resolution images and the reorienting of the one or more remaining constituent visualization components.

15. The method of claim 10, wherein constructing, by the at least a processor, the plurality of virtual images as a function of the image data set further comprises:

determining a spatial distance between each reference constituent visualization and one or more remaining virtual constituent components for each image of the plurality of images; and constructing at least one virtual image of the plurality of virtual images as a function of the spatial distance.

16. The method of claim 10, wherein constructing, by the at least a processor, a plurality of virtual images as a function of the image data set further comprises:

identifying one or more annotations on at least one image of the plurality of images;

receiving one or more configurable parameters of the plurality of images; and removing the one or more annotations as a function of the one or more configurable parameters.

17. The method of claim 16, wherein the one or more configurable parameters are received as a function of user input.

18. The method of claim 10, wherein determining, by the at least a processor, a relationship between one or more constituent visualization components comprises identifying one or more constituent visualization components using an image processing module.

* * * * *